(12) United States Patent
Mule

(10) Patent No.: US 9,234,175 B2
(45) Date of Patent: Jan. 12, 2016

(54) CREATING BIOENGINEERED LYMPH NODES

(75) Inventor: James J. Mule, Odessa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 283 days.

(21) Appl. No.: 13/508,305

(22) PCT Filed: Nov. 16, 2010

(86) PCT No.: PCT/US2010/056866
§ 371 (c)(1),
(2), (4) Date: May 31, 2012

(87) PCT Pub. No.: WO2011/062909
PCT Pub. Date: May 26, 2011

(65) Prior Publication Data
US 2012/0244181 A1 Sep. 27, 2012

Related U.S. Application Data

(60) Provisional application No. 61/261,945, filed on Nov. 17, 2009.

(51) Int. Cl.
| | |
|---|---|
| C12N 5/071 | (2010.01) |
| C12N 15/86 | (2006.01) |
| C12N 15/74 | (2006.01) |
| C12N 15/87 | (2006.01) |
| C12N 5/0784 | (2010.01) |
| C07K 14/52 | (2006.01) |
| A61K 35/12 | (2015.01) |

(52) U.S. Cl.
CPC ............ *C12N 5/0639* (2013.01); *C07K 14/521* (2013.01); *A61K 35/12* (2013.01)

(58) Field of Classification Search
None
See application file for complete search history.

(56) References Cited

U.S. PATENT DOCUMENTS

| | | |
|---|---|---|
| 8,101,195 B2 | 1/2012 | Watanabe et al. |
| 2004/0175355 A1 | 9/2004 | Dubinett et al. |
| 2007/0015136 A1 | 1/2007 | Sanchez-Schmitz |

OTHER PUBLICATIONS

Sallusto et al., 1999, Eur. J. Immunol. vol. 29: 1617-1625.*
Riedl et al., 2003, Mol. Canc. vol. 2: 1-13.*
Moser et al.,2004, Ann Rheum. Dis 63: 84-89.*
Means et al., 2003, J. Immunol. vol. 170: 5165-5175.*
Harlin et al., "Chemokine Expression in Melanoma Metastases Associated with CD8+T-Cell Recruitment," *Cancer Res.*, 69(7):3077-85, 2009.
Henry et al., "IL-12 Produced by Dendritic Cells Augments CD8+T Cell Activation Through the Production of the Chemokines CCL1 and CCL17," *J Immunol.*, 181(12):8576-84, 2008.
Huang et al., "The Neuronal Chemokine CX3CL1/Fractalkine Selectively Recruits NK Cells That Modify Experimental Autoimmune Encephalomyelitis Within the Central Nervous System," *FASEB 1*, 20(7):896-905, 2006.
Jicha et al., Interleukin 7 Generates Antitumor Cytotoxic T Lymphocytes Against Murine Sarcomas with Efficacy in Cellular Adoptive Immunotherapy, *J. Exp Med.*, 174(6):1511-5, 1991.
Kirk et al., "The Dynamics of the T-Cell Antitumor Response: Chemokine-Secreting Dendritic Cells Can Prime Tumor-Reactive T Cells Extranodally," *Cancer Res,.* 61(24):8794-8802, 2001.
Kirk et al., "T Cell-Dependent Antitumor Immunity Mediated by Secondary Lymphoid Tissue Chemokine: Augmentation of Dendritic Cell-Based Immunotherapy," *Cancer Res,.* 61(5):2062-70, 2001.
Kirk and Mulé, Gene-Modified Dendritic Cells for Use in Tumor Vaccines, *Hum Gene Ther.*, 11(6):797-806, 2000.
Klebanoff et al., "IL-15 Enhances the *in vivo* Antitumor Activity of Tumor-Reactive CD8+T Cells," *Proc Natl Acad Sci*, 101(7):1969-74, 2004.
Klebanoff et al., "Central Memory Self/Tumor-Reactive CD8+T Cells Confer Superior Antitumor Immunity compared with Effector Memory T Cells," *Proc Natl Acad Sci.*, 102(27):9571-9576, 2005.
Lai et al., "Mouse Cell Surface Antigens: Nomenclature and Immunophenotyping,". *J Immunol.* 160(8):3861-8, 1998.
Lambert et al., "Intranodal Immunization with Tumor Lysate-Pulsed Dendritic Cells Enhances Protective Antitumor Immunity," *Cancer Res.*, 61(2):641-6, 2001.
Legler et al, B Cell-Attracting Chemokine 1, a Human CXC Chemokine Expressed in Lymphoid Tissues, Selectively Attracts B Lymphocytes via BLR1/CXCR5. *J Exp Med.*, 187(4):655-60, 1998.
Lehmann et a., "Clinical Response to the MAGE-A3 Immunotherapeutic in Metastatic Melanoma Patients is Associated with a Specific Gene Profile Present Prior to Treatment," *Cancer Immunity*, 8:Suppl 2, 27, 2008.
Louahed et al., "Expression of Defined Genes Identified by Pretreatment Tumor Profiling: Association with Clinical Responses to the GSK MAGE—A3 Immunotherapeutic in Metastatic Melanoma Patients (EORTC 16032-18031)," *J Clin Oncol.*, 26: 9045, 2008 (Abstract).
Maghazachi and Al-Aoukaty, "Chemokines Activate Natural Killer Cells Through Heterotrimeric G-Proteins: Implications for the Treatment of Aids and Cancer," *FASEB J.*, 12(11):913-24, 1998.
Matsumura et al., "Radiation-Induced CXCL16 Released by Breast Cancer Cells Attracts Effector T Cells," *J Immunol.* 181(5):3099-107, 2008.
Morse et al., "Migration of Human Dendritic Cells After Injection in Patients with Metastatic Malignancies," *Cancer Res.*, 59(1):56-8, 1999.
Muléet al., "RANTES: Secretion by Gene-Modified Tumor Cells Results in Loss of Tumorigenicity *In Vivo*: Role of Immune Cell Subpopulation," *Hum Gene Ther.*, 7(13):1545-1553, 1996.
Mullins and Engelhard, "Limited Infiltration of Exogenous Dendritic Cells and Naïve T Cells Restricts Immune Responses in Peripheral Lymph Nodes," *J Immunol.*, 176(8):4535-42, 2006.
Nakahara et al., "Effect of Inhibition of Vascular Endothelial Growth Factor Signaling on Distribution of Extravasated Antibodies in Tumors," *Cancer Res.*, 66(3):1434-45, 2006.

(Continued)

*Primary Examiner* — Amy Juedes
(74) *Attorney, Agent, or Firm* — Fish & Richardson P.C.

(57) ABSTRACT

The invention provides compositions and methods of treating various conditions, including tumors, with compositions comprising dendritic cells expressing exogenous chemokines.

26 Claims, 15 Drawing Sheets

(56) References Cited

OTHER PUBLICATIONS

Novak et al., "Characterization of the CCL21-Mediated Melanoma-Specific Immune Responses and *in situ* Melanoma Eradication," *Mol Cancer Ther.*, 6(6): 1755-64, 2007.
Overwijk et al., "Tumor Regression and Autoimmunity After Reversal of a Functionally Tolerant State of Self-Reactive CD8+T Cells," *J Exp Med.*, 198(4):569-80, 2003.
Overwijk et al., "gp 100/pmel 17 Is a Murine Tumor Rejection Antigen: Induction of "Self"—Reactive, Tumoricidal T Cells Using High-Affinity, Altered Peptide Ligand," *J Exp Med.*, 188(2):277-86, 1998.
Pan et al., "CXCR3/CXCR3 Ligand Biological Axis Impairs RENCA Tumor Growth by a Mechanism of Immunoangiostasis," *J Immunol.* 176(3): 1456-64, 2006.
Reschner et al., "Innate Lymphocyte and Dendritic Cell Cross-Talk: A Key Factor in the Regulation of the Immune Response," *Clin Exp Immunol.* 152(2):219-26, 2008.
Selvakumaran et al., "Role of CCL19 and CCL21 Chemokines in the Response of Ovarian Tumors to Platinum-Based Chemotherapy," *Proc Amer Assoc Cancer Res.*, vol. 45, Abstract nr 1472, 2004.
Sfondrini et al., "High Level Antibody Response to Retrovirus-Associated But Not to Melanocyte Lineage-Specific Antigens in Mice Protected Against B16 Melanoma," *Int J Cancer*. 83(1):107-12, 1999.
Shurin et al., "Loss of New Chemokine CXCL14 in Tumor Tissue is Associated with Low Infiltration by Dendritic Cells (DC), While Restoration of Human CXCL14 Expression in Tumor Cells Causes Attraction of DC Both In Vitro and in Vivo," *J Immunol.*, 174(9):5490-8, 2005.
Terando et al., "Chemokine Gene Modification of Human Dendritic Cell-Based Tumor Vaccines Using a Recombinant Adenoviral Vector," *Cancer Gene Ther*. 11(3):165-173, 2004.
Thanarajasingam et al., "Delivery of CCL21 to Metastatic disease Improves the Efficacy of Adoptive T-Cell Therapy," *Cancer Res*. 67(1):300-8, 2007.
van de Pavert et al., "Chemokine CXCL13 is Essential for Lymph Node Initiation and is Induced by Retinoic Acid and Neuronal Stimulation," *Nature Immun.*, 10(11) 1193-1200, 2009.
Vansteenkiste et al., "Association of Gene Expression Signature and Clinical Efficacy of MAGE-A3 Antigen-Specific Cancer Immunotherapeutic (ASCI) as Adjuvant Therapy in Resected Stage IB/II Non-Small Cell Lung Cancer (NSCLC)," *J Clin Oncol*, 26: 7501, 2008 (Abstract).
Verdijk et al., "Maximizing Dendritic Cell Migration in Cancer Immunotherapy," *Expert Opin Bio Ther.*, 8(7):865-74, 2008.
Winter et al., "Therapeutic T Cells Induce Tumor-Directed Chemotaxis of Innate Immune Cells Through Tumor-Specific Secretion of Chemokines and Stimulation of B16BL6 Melanoma to Secrete Chemokines," *J Transl Med.*, 5:56, 2007.
Wu et al., "Tumor Transfected with CCL21 Enhanced Reactivity and Apoptosis Resistance of Human Monocyte-Derived Dendritic Cells," *Immunobiology*, 213(5):417-26, 2008.
Yamazaki et al., "CCR6 Regulates the Migration of Inflammatory and Regulatory T Cells," *J Immunology*, 181(12):8391-401, 2008.
Yang et al., "Intrapulmonary Administration of CCL21 Gene-Modified Dendritic Cells Reduces Tumor Burden in Spontaneous Murine Bronchoalveolar Cell Carcinoma," *Cancer Research*, 66(6):320513, 2006.
Yousefieh et al., "Gene Therapy: $CCL_{21}$ (SLC) Inhibits Primary Prostate Tumor Growth and Metastases," *FASEB Journal*, 22: 1076.15, 2008.
Zhang et al., "CXC Chemokine Ligand 12 (Stromal Cell-Derived Factor 1 α) and CXCR4-Dependent Migration of CTLs Toward Melanoma Cells in Organotypic Culture," *J Immunol*. 174(9):5856-63, 2005.
Zitvogel et al., "Dendritic Cell-NK Cell Cross-Talk: Regulation and Physiopathology," *Curr Top Microbiol Immunol.*, 298: 157-74, 2006.
Dubois et al., "Selective attraction of naive and memory B cells by dendritic cells," Journal of Leukocyte Biology 70:633-641, 2001.
International Search Report and Written Opinion; Application No. PCT/US2010/056866; Applicant: H. Lee Moffitt Cancer Center and Research Institute, Inc. et al.: mailed Jul. 18, 2011 (13 pages).
Matsuyoshi et al., "Therapeutic effect of alpha-galactosylceramide-loaded dendritic cells genetically engineered to express SLC/CCL21 along with tumor antigen against peritoneally disseminated tumor cells," Cancer Science 96:889-896, 2005.
Megjugorac et al., "Virally stimulated plasmacytoid dendritic cells produce chemokines and induce migration of T and NK cells," Journal of Leukocyte Biology 75:504-514, 2004.
Adema et al., "Migration of Dendritic Cell Based Cancer Vaccines: In Vivo Veritas?" *Curr Opin Immunol*, 17(2): 170-4, 2005.
Ashour et al., "CCL21 Is an Effective Surgical Neoadjuvant for Treatment of Mammary Tumors," *Cancer Bio. Ther.*, 6(8):1206-10, 2007.
Bacon et al., "Activation of Dual T Cell Signaling Pathways by the Chemokine RANTES," *Science*, 269(5231):1727-30, 1995.
Barth et al., "Unique Murine Tumor-Associated Antigens Identified by Tumor Infiltrating Lymphocytes,".*J Immuno*,. 144(4): 1531-7, 1990.
Brown et al., "Tumor-Derived Chemokine MCP-1ICCL2 is Sufficient for Mediating Tumor Tropism of Adoptively Transferred T Cells," *J Immunol*, 179(5):3332-41, 2007.
Chang et al., "A Phase I Trial of Tumor Lysate-Pulsed Dendritic Cells in the Treatment of Advanced Cancer," *Clin Cancer Res*, S(4):1021-32, 2002.
Chen et al., Heat Shock Protein 70, Released from heat-Stressed Tumor Cells, Initiates Antitumor Immunity by Inducing Tumor Cell Chemokine Production and Activating Dendritic Cells via TLR4 Pathway, *J Immunol*, 182(3):1449-59, 2009.
Coppola et al., "Ectopic Lymphoid Tissue in Colonic Adenocarcinoma," [abstract] In: Proceedings of the lOOth Annual Meeting of the American Association for Cancer Research; Apr. 18-22, 2009; Denver, CO. Philadelphia (PA): AACR; 2009. Late Breaking Abstract nr 9047.
Coppola and Mule JJ, Ectopic Lymph Nodes Within Human Solid Tumors, *J Clin Oncol.*, 26(27):4369-70, 2008.
Eggert et al., "Biodistribution and Vaccine Efficiency of Murine Dendritic Cells are Dependent on the Route of Administration," *Cancer Res.*, 59(14):3340-5, 1999.
Eisenthal et al., "Effect of Anti-B16 Melanoma Monoclonal Antibody on Established Murine B16 Melanoma Liver Metastases," *Cancer Res.*, 47(11):2771-6, 1987.
Fedorovskaia et al., "Antibodies Against Cells of Methylcholanthrene Sarcoma In the Blood of Intact Mice," *Biull Eksp Bio Med.*, 76(7):7880, 1973.
Fernandez et al., "Dendritic Cells Directly Trigger NK Cell Functions: Cross-Talk Relevant in Innate Anti-Tumor Immune Responses *in vivo*," *Nat Med.*, 5(4):405-11, 1999.
Gajewski, "Insights into Mechanisms of Immune Resistance in the Tumor Microenvironment through Molecular Profiling," *Innate and Adaptive Immunity in the Tumor Microenvironment*, vol. 1. Netherlands: Springer; p. 77-89, 2008.
Geiger et al., Vaccination of Pediatric Solid Tumor Patients with Tumor Lysate-Pulsed Dendritic *Cells Cancer Res.*, 61(23):8513-9, 2001.
Gorbachev et al., "CXC Chemokine Ligand 9/Monokine Induced by IFN-γ. Production by Tumor Cells Is Critical for T Cell-Mediated Suppression of Cutaneous Tumors," *J Immunol.*, 178(4):227886, 2007.

* cited by examiner

Ectopic Lymph Node Structures in Lung Adenocarcinoma

Case 1: CD20+ B cell follicles     Case 1: CD3+ T cell marginal zones

Case 2: CD3+ T cells in marginal zone and in follicle within colon tumor x20

Case 2: CD20+ B cells in center of follicle within colon tumor x20

Case 3: CD20 expression is negative in colon tumor x20

Case 3: CD3+ T cells are dispersed within the colon tumor x20

Ectopic Lymph Node Structures in Melanoma
(Case 4)

CREATING BIOENGINEERED LYMPH NODES

CLAIM OF PRIORITY

This application is a U.S. National Phase Application of International Patent Application No. PCT/US2010/056866 filed Nov. 16, 2010, entitled "CREATING BIOENGINEERED LYMPH NODES," which claims the benefit of U.S. Patent Application Ser. No. 61/261,945, filed on Nov. 17, 2009, the entire contents of which are hereby incorporated by reference.

FEDERALLY SPONSORED RESEARCH OR DEVELOPMENT

This invention was made with Government support under Grant No. CA059327 awarded by the National Institutes of Health. The Government has certain rights in the invention.

TECHNICAL FIELD

This invention relates to cancer treatment and the treatment of diseases associated with immune responses characterized by innate and adaptive immunity. More specifically, this invention relates to bioengineered dendritic cells (DC) that express one or more chemokines, and can be loaded with tumor antigens or other antigens associated with disease. When injected in vivo, these bioengineered DC create a functioning lymph node-like structure(s) at the site(s) of their injection.

BACKGROUND

Ex vivo generated dendritic cells (DC) in both mouse and humans have very limited movement from subcutaneous or intradermal injection sites to locally draining lymph node(s) and essentially none to spleen (Chang et al., Clin Cancer Res. 8(4):1021-32, 2002; Geiger J D, et al., Cancer Res. 61(23): 8513-9, 2001.). This limitation is considered to be one of the significant weaknesses in the use of DC-based vaccines to date. It is also clear that the intravenous route of administration of DC has proven ineffective to target multiple peripheral lymphoid organs. Most DC administered by this route appear to be trapped rapidly in the capillaries of the lungs, in the spleen, and in the liver where the DC tend to be cleared. Immunization by this route is generally inadequate and some investigators have abandoned the intravenous delivery of DC both in animal studies and in human clinical trials. Recently, the direct intranodal delivery of antigen-loaded DC has gained much favor, as this route appears to be somewhat superior for inducing immune responses compared to the subcutaneous or intradermal route (Adema et al., Curr Opin Immunol. 17(2):170-4, 2005.; Verdijk et al., Expert Opin Biol Ther. 8(7):865-74, 2008.; Lambert et al., Cancer Res. 61(2): 641-6, 2001.). However, it is logistically and technically impractical to deliver a large number of DC to a single lymph node, especially in the setting of chemotherapy-induced shrinkage, as well as to target multiple lymph nodes by the current methodology.

SUMMARY

Antigen-presenting cells (APCs) and lymphocyte effectors are both required for an effective immune response to an antigen (see, e.g., Huang et al., Science 264:961-965, 1994). Intact, whole tumor cells are ineffective APCs because they often have low antigen(s) expression, limited expression of MHC antigens, and lack costimulatory molecules (see, e.g., Restifo et al., J. Exp. Med. 177:265-272, 1993). Further, viable tumor cells secrete immunosuppressive mediators to evade the host immune response (Huang et al., Cancer Res. 58:1208-1216, 1998; Sharma et al., J. Immunol. 163:5020-5028, 1999; and Uzzo et al., J. Clin. Investig. 104:769-776, 1999). Described herein are compositions and methods using ex vivo generated, chemokine(s)-expressing DC that are effective to attract and activate selective immune cells in vivo, and, by doing so, create a functioning lymph node-like structure(s) at the site(s) of their injection.

In one aspect, the invention features compositions including DC (e.g., $CD14^+$ blood monocyte-derived DC, dermal or interstitial dendritic cells, Langerhans cells, and/or plasmacytoid DC) expressing one or more exogenous chemokines that attract and/or increase activation of lymphocytes (e.g., $CD4^+/CD8^+$ T cells, natural killer (NK) cells, and B cells) and/or other immune cells (e.g., monocytes/macrophages and other endogenous DC) if so desired. In some embodiments, the cells express (i) at least one exogenous chemokine that attracts or increases activation of CD4+/CD8+ T cells; (ii) at least one exogenous chemokine that attracts or increases activation of natural killer (NK) cells; and (iii) at least one exogenous chemokine that attracts or increases activation of B cells. The DC can be loaded with an antigen (e.g., tumor, viral, bacterial, or fungal antigens).

In another aspect, the invention features a population of DC (e.g., CD14+ blood monocyte-derived DC, dermal or interstitial dendritic cells, Langerhans cells, and/or plasmacytoid DC) expressing exogenous chemokines that attract and/or increase activation of at least two, or more of $CD4^+/CD8^+$ T cells, NK cells, and B cells. In some embodiments, the invention features mixed populations of DC expressing exogenous chemokines that attract or increase activation of at least two, or more of $CD4^+/CD8^+$ T cells, NK cells, and B cells. In some embodiments, the cells all express multiple exogenous chemokines, e.g., same chemokines or different chemokines. In some embodiments, the cells express one exogenous chemokine, but cells in the population of cells express two or more exogenous chemokines.

In some embodiments, the DC expresses at least one exogenous chemokine that attracts or increases activation of T cells that is selected from within the classes C, CC, CXC, and CX3C, e.g., as shown in Table 2. In some embodiments, the DC expresses one or more exogenous chemokines that attract and/or increase activation of T cells, e.g., CCL-1, CCL-2, CCL-3, CCL-4, CCL-5, CCL-8, CCL-13, CCL-17, CCL-18, CCL-20, CCL-21, CXCL-9, CXCL-10, CXCL-11, CXCL-14, CXCL-16, and XCL1.

In some embodiments, the DC expresses at least one exogenous chemokine that attracts or increases activation of NK cells that is selected from within the classes C, CC, CXC, and CX3C, e.g., as shown in Table 2, e.g., CCL-8 and CX3CL-1.

In some embodiments, the DC expresses at least one exogenous chemokine that attracts or increases activation of B cells selected from within the classes C, CC, CXC, and CX3C, e.g., as shown in Table 2, e.g., CCL-8, CCL-18, and CXCL-13.

In some embodiments, the dendritic cell expresses exogenous chemokines from within the classes C, CC, CXC, and CX3C, e.g., as shown in Table 2

In some embodiments, the invention provides DC expressing CCL-21 and at least one other chemokine. In some embodiments, the dendritic cells express CCL-21, CX3CL-1, and CXCL-13.

In yet another aspect, the invention provides methods of treating or inhibiting, or reducing risk of developing, cancer or a viral, bacterial, or fungal infection in a subject. The methods can include selecting a subject that has, or is at risk of developing, cancer, or a viral, bacterial, or fungal infection. The methods also can include administering a therapeutically effective amount of a composition or population of chemokine-expressing DC.

In a further aspect of the invention, methods of creating a bioengineered lymph node structure in a subject are provided. The methods can include providing a composition or population of chemokine-expressing DC as described herein that are loaded with an antigen(s) (e.g., tumor, viral, bacterial, or fungal antigens) and injecting the chemokine-expressing, antigen(s)-loaded DC into a subject.

Also provided herein are the compositions and populations of cells as described herein for treating or inhibiting cancer, or a viral, bacterial, or fungal infection in a subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
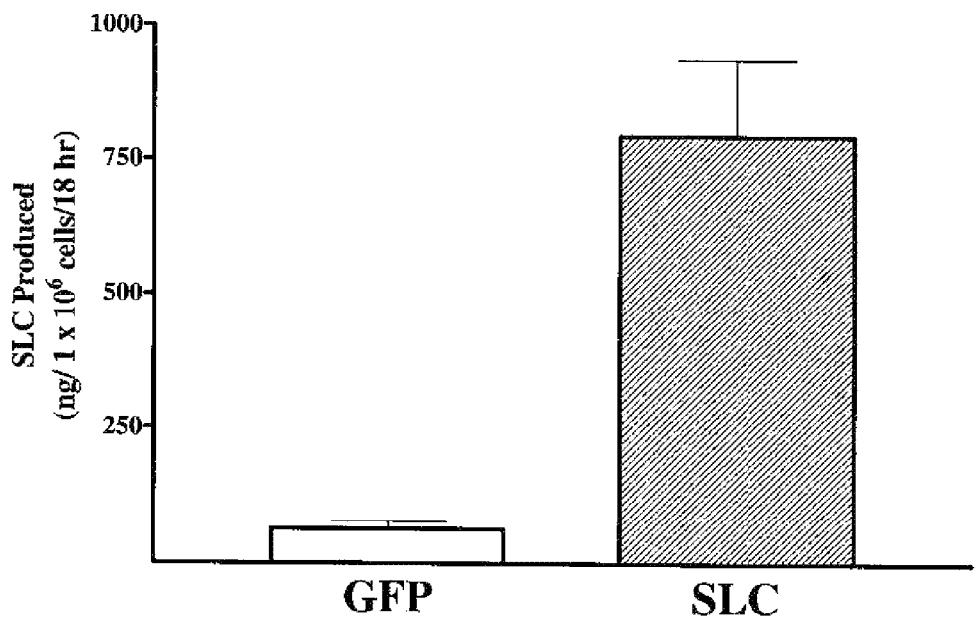
FIG. 1 is a bar graph showing the means of the amount of CCL-21 (also denoted SLC) produced in 18 hours by $1\times10^6$ genetically modified DC and is cumulative of nine separate infections; bars, SE. DC were harvested from 4- to 6-day-old bone marrow cultures and infected with adenoviral vectors encoding for either SLC/CCL-21 or GFP. Supernatants were harvested 18 hours after infection and were used in the bottom chamber of a 24-well plate microchemotaxis assay; CD4$^+$ T cells from splenocytes served as responders. Recombinant SLC/CCL-21 (10-5000 ng/ml) was used to generate a standard curve from which the effective concentration of SLC/CCL-21 in the cultured supernatants was determined. Duplicate to quadruplicate samples were run for each supernatant tested.

It has been shown that limited infiltration of exogenous dendritic cells (DC) and naïve T cells restricts immune responses in peripheral lymph nodes (Mullins and Engelhard, J. Immunol. 176(8):4535-42, 2006.). Rather than focusing on attempts to deliver greater numbers of ex vivo generated DC to lymph nodes, the present methods attract selected immune cells to the site(s) of administered DC through the use of chemokines.

Chemokines, which are small protein molecules involved in immune and inflammatory responses, direct leukocyte trafficking to areas of injury as well as to locations where primary immune responses are initiated (secondary lymphoid tissues such as lymph nodes, spleen, Peyer's patches, and tonsils). There are presently four classes of chemokine molecules (C, CC, CXC, and $CX_3C$) that are named for the number and location of cysteine residues on the amino terminus of the protein. These molecules communicate with their target cells via G-protein coupled receptors that are pertussis toxin sensitive. Different chemokines act on different leukocyte populations, thereby modulating the influx of immune effector cells to the area in question based on the needs of the particular situation. Various chemokines have been identified that have profound activities on the antitumor immune response. As examples, tumor-derived, heat shock protein 70 can initiate antitumor immunity by inducing chemokine production (Chen et al., J. Immunol. 182(3):1449-59, 2009.), IL-12 produced by dendritic cells can augment $CD8^+$ T cell activation through the production of CCL-1 and CCL-17 (Henry et al., J. Immunol. 181(12):8576-84, 2008.), CCL-20 can regulate the migration of inflammatory and regulatory T cells (Yamazaki et al., J. Immunol. 181(12):8391-401, 2008.), CCL-2 can mediate tumor tropism of adoptively transferred T cells (Brown et al., J. Immunol. 179(5):3332-41, 2007.), CXCL-9 induced by IFN-γ production by tumor cells is critical for T cell-mediated suppression of cutaneous tumors (Gorbachev et al., J. Immunol. 178(4):2278-86, 2007), CXCL-14 expression in tumor cells can cause attraction of DC in vivo (Shurin et al., J. Immunol. 174(9):5490-8, 2005.), CXCL-12 can mediate the migration of cytotoxic T cells (CTL) toward melanoma resulting in tumor regression (Zhang et al., J. Immunol. 174(9):5856-63, 2005.), CXCL-9 combined with systemic IL-2 can inhibit tumor growth by increased intratumor infiltration of $CXCR3^+$ mononuclear cells (Pan et al., J. Immunol. 176(3):1456-64, 2006.), radiation-induced CXCL-16 release by breast cancer cells can attract effector T cells and elicit tumor regression (Matsumura et al., J. Immunol. 181(5):3099-107, 2008.), and therapeutic T cells can induce tumor-directed chemotaxis of innate immune cells through tumor-specific secretion of CCL-3, CCL-4, and CCL-5 (Winter et al., J Transl Med. 5:56, 2007.). Moreover, chemokine genes have been identified as key elements of molecular signatures that appear to be predictive of clinical efficacy of immunotherapy in melanoma (Harlin et al., Cancer Res. 69(7):3077-85, 2009.; Gajewski, "Insights into Mechanisms of Immune Resistance in the Tumor Microenvironment through Molecular Profiling." In: Yefenof E, editor. Innate and Adaptive Immunity in the Tumor Microenvironment, Vol 1. Netherlands: Springer; 2008. p. 77-89.; Lehmann et al., Clinical response to the MAGE-A3 immunotherapeutic in metastatic melanoma patients is associated with a specific gene profile present prior to treatment. Cancer Immunity. 8:suppl 2, 27, 2008 (Meeting Abstract).; Louahed et al., Expression of defined genes identified by pretreatment tumor profiling: Association with clinical responses to the GSK MAGE-A3 immunotherapeutic in metastatic melanoma patients (EORTC 16032-18031). J Clin Oncol 26: 9045, 2008 (Abstract).) and non-small cell lung cancer (Vansteenkiste et al., J Clin Oncol 26: 7501, 2008 (Abstract).). In addition, in situ expression of certain chemokines can be linked to the appearance of ectopic lymph node-like structures within solid tumor masses, which appear to correlate with better prognosis (Coppola et al., Ectopic lymphoid tissue in colonic adenocarcinoma. [abstract]. In: Proceedings of the 100th Annual Meeting of the American Association for Cancer Research; 2009 Apr. 18-22; Denver, Colo. Philadelphia (PA): AACR; 2009. Late Breaking Abstract nr 9047.; Coppola and Mulé, J Clin Oncol. 26(27):4369-70, 2008.).

Some previous efforts to induce antitumor immunity involved stably transducing tumors to express the chemokine of interest. Antitumor immunity was successfully generated when tumors were transduced to produce RANTES, a CC chemokine now denoted CCL-5 (Mulé et al., Hum Gene Ther. 7(13):1545-53, 1996.). This effect was attributable, at least partially, to the recruitment of monocytes and T cells to the tumor site. Similar effects of lymphocyte effector recruitment have been seen subsequently by other investigators using Mig (CXCL9) and Lymphotactin (XCL1) among others (Kirk and Mulé, Human Gene Ther. 11:797-806, 2000; Terando and Mulé, Blood Cells, Molecules, and Diseases. 31:80-83, 2003). At least two shortcomings of this approach, however, are that it is dependent on the creation of a gene-modified tumor in order to initiate an antitumor response, which first requires removal and manipulation of an often limited number of viable tumor cells ex vivo, and relies entirely on the inherent immunogenicity of that tumor for successful immune priming.

CCL-21 (also denoted SLC, Exodus-2, thymus-derived chemotactic agent 4, 6CKine) is a CC chemokine found in the high endothelial venules of the lymph node (Kirk et al., Cancer Res. 61(5):2062-70, 2001.; Kirk et al., Cancer Res. 61(24):8794-802, 2001.; Terando et al., Cancer Gene Ther. 11(3):165-73, 2004.; Kirk and Mulé, Hum Gene Ther. 11(6): 797-806, 2000.). It was initially reported to be a chemoattractant specifically for naïve T lymphocytes and DC. As described herein, genetically modifying mouse tumor antigen(s)-pulsed DC (TL-DC) to produce SLC/CCL-21, naïve T cells were specifically recruited to the site of TL-DC injection in the skin by creating a new bioengineered lymph node structure that is, importantly, functional (i.e., the TL-DC in the bioengineered node served as antigen presenting cells to "educate" the large numbers of arriving naïve T cells that were recruited to the site by the local production of SLC/CCL-21). In this case, "structure" is defined histologically by the dense accumulation of immune cells with the presence of dendritic cells as APC, without a definable capsule and without high endothelial venules (HEVs). When naïve T cells encountered TL-DC at the vaccination site, the TL-DC interacted with the naïve T cells through costimulatory and MHC Class I and II molecules, thus initiating a primary immune response that then created a powerful systemic antitumor immunity (as the "educated" T cells egressed from the local site and systemically disseminated through the peripheral lymphoid system and blood) that caused regression of local tumor at or near the skin injection site in addition to metastatic disease at distant, visceral sites. Thus, SLC/CCL-21 could both induce antitumor responses and enhance the antitumor immunity elicited by TL-DC in vivo. Also, direct administration of DC genetically modified to express SLC/CCL-21 into growing tumors themselves could result in a substantial, sustained influx of T cells within the mass with only a transient increase in T cell numbers in the draining lymph node (DLN). TL-DC were retained at the tumor site with only a very small percentage trafficking to the DLN. The T cells infiltrating the tumor mass expressed the activation marker CD25 within 24 hours and developed IFN-gamma-secreting function specifically to the tumor within 7 days as tumor growth became inhibited. Importantly, similar results were obtained in lymphotoxin-alpha gene knock out (Ltα-/-) mice, which completely lacked peripheral lymph nodes. These data demonstrated for the first time that effective T cell priming could occur extranodally and result in measurable, enhanced antitumor effects in vivo, through creation of new, functional bioengineered lymph node structures.

Human TL-DC that are genetically modified to secrete human SLC/CCL-21, similar to the murine studies, may be expected to potently recruit naïve human CD4$^+$ and CD8$^+$ T cells (in this instance in vitro; Terando et al., Cancer Gene Ther. 11(3):165-73, 2004.). Importantly, TL-DC secreting the SLC/CCL-21 could also significantly enhance the level/number of tumor antigen-specific T cells to at least two, specific melanoma peptides (i.e., MART-1 and gp100). Thus, TL-DC producing SLC/CCL-21 served as a vehicle for both recruiting naïve T cells and enhancing the production of tumor-specific T cells.

Murine TL-DC can elicit tumor-specific T cell reactivities in vitro and in vivo. This observation has been made in a variety of histologically-distinct murine tumors, including sarcoma, carcinoma, and melanoma. Syngeneic hosts can be effectively immunized in vivo to reject aggressive, weakly-immunogenic sarcomas, a breast carcinoma, and a poorly-immunogenic subline of the B16 melanoma by immunization with TL-DC, which is dependent upon host-derived CD8$^+$ and CD4$^+$ T cells. TL-DC treatments can, under certain circumstances, also result in regression of both established subcutaneous tumor nodules and lung metastases. Gene-modification of TL-DC to produce a SLC/CCL-21 can enhance vaccine efficacy and inhibit tumor growth by priming tumor-reactive T cells extranodally.

Engineered DC

The present disclosure, in some aspects, provides DC or populations of DC singly or pooled that are engineered to express one, two, or more exogenous chemokines and are optionally loaded with an antigen (e.g., a tumor, viral, bacterial, or fungal antigen). The administration of these engineered DC initiates the induction in a patient of a functional lymph node-like structure at the site of their injection. The lymph node-like structure is formed as a result of the recruitment of various types of immune cells to the site of injection of the engineered DC; the latter also activates the recruited immune cells to increase their numbers and their response to the antigen. The activated immune cells then migrate to the site(s) of disease, e.g., a tumor, in the patient and cause the antigen-expressing cells, e.g., tumor cells, to be killed and the tumor mass(es) to regress.

The production of the chemokine-expressing, antigen-loaded DC can involve a multi-step process, which is also described herein.

An initial step of the process is to select chemokine(s) that enhance the migration of the desired immune cell types, e.g., naïve T cells (both CD4$^+$ and CD8$^+$), T central memory cells (Tcm), T effector memory cells (Tem), natural killer (NK) cells, immature and mature DC, and B cells, but generally do not attract suppressive T regulatory cells (Treg). Each cell type migrates in response to different chemokines, hence, the first step is to identify the chemokines that best attract the desired immune cells. Single and multiple chemokines are then selected for further screening in vivo for creation of functioning bioengineered lymph node structures in mice with the intent of taking the leads from this preclinical exercise into humans.

An additional step of the process is to select a particular antigen that is to be loaded onto DC. For some tumors, an appropriate single molecular antigen is known and selected. For other antigens, a complex mixture may be selected, such as killed tumor cells or a fraction thereof, e.g., a fraction comprising plasma membranes of the tumor cells.

Another step of the process is the introduction into DC of one or more recombinant vectors that express the one or more chemokines associated with the immune cell types of interest.

A further step of the process is to load the chemokine-expressing DC with the antigen of interest (where the antigen is loaded onto the DC).

The final step is to inject the chemokine-expressing, tumor antigen-loaded (TL-)DC into a patient, to create a bioengineered lymph node structure.

These methods are used to create chemokine-producing, TL-DC (e.g., a single TL-DC producing a single chemokine, a single TL-DC producing multiple chemokines, or a population of multiple TL-DC combined where the TL-DC in the mixture can each produce one or more chemokine and wherein the population as a whole produces multiple chemokines). These engineered DC, when injected, induce a functioning bioengineered lymph node structure in the skin, whereby the chemokines are believed to attract and concentrate immune cell subsets, and the TL-DC, as the antigen presenting cells, activate the accumulating immune cell subsets, and the chemokines also serve to enhance functional activity of the responding immune cell subsets. The approach includes the option of injecting the pooled chemokine(s)-producing TL-DC at multiple, independent sites to potentially create multiple, independent functioning lymph node-like structures concurrently. The injections can also be staggered to create additional new structures over time. These structures should prove to act independently of each other, raising the option of creating completely different functioning lymph node-like structures in the same person or animal by injecting pools of different chemokine(s)-producing TL-DC. Moreover, the approach can be supplemented by adoptive transfers of additional, freshly prepared (preferably autologous) immune cell subsets given i.v. to further augment the creation/size/function of lymph node-like structures and/or immunity by their recruitment from circulation to the injection site.

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid, or viral vector. The vector can be capable of autonomous replication or it can integrate into a host DNA. Viral vectors include, e.g., replication defective retroviruses, adenoviruses, and adeno-associated viruses.

A vector can include a nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers, and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides encoded by nucleic acids as described herein.

When used in mammalian cells, the expression vector's control functions are often provided by viral regulatory elements. For example, commonly used promoters are derived from polyoma, Adenovirus 2, cytomegalovirus, and Simian Virus 40.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

The overview above has been presented in the context of tumor antigen. It should be understood that the invention is not limited to the induction of a functional lymph node-like structure for treating tumors and using tumor antigens, but would be extendable to other antigens, such as viral, bacterial, or fungal antigens to treat infections. In addition, the steps need not be performed in the order set forth above, and in some embodiments, not all steps need to be performed.

Immune Cells

T lymphocytes are usually divided into two major subsets that are functionally and phenotypically distinct. The $CD4^+$ T cell, is a pertinent coordinator of immune regulation. The main function of the $CD4^+$ T cell is to augment or potentiate immune responses by the secretion of chemokines that activate other white blood cells to fight off infection. Another important type of T cell is the $CD8^+$ T cell. These cells are important in directly killing certain tumor cells, pathogen-infected cells, and sometimes parasites. The $CD8^+$ T cells are also important in down-regulation of immune responses. Both types of T cells can be found throughout the body. They often depend on the secondary lymphoid organs (the lymph nodes and spleen) as sites where activation occurs, but they are also found in other tissues of the body, most conspicuously the liver, lung, blood, and intestinal and reproductive tracts.

NK cells are similar to the killer T cell subset ($CD8^+$ T cells). They function as effector cells that directly kill certain tumors such as melanomas, lymphomas, and pathogen-infected cells, most notably herpes and cytomegalovirus-infected cells. NK cells, unlike the $CD8^+$ T cells, kill their targets without a prior activation in the lymphoid organs. However, NK cells that have been activated by chemokines secreted from $CD4^+$ T cells will kill their tumor or pathogen-infected targets more effectively.

The major function of B lymphocytes is the production of antibodies in response to foreign proteins of tumor cells, viruses, bacteria, and fungi. Antibodies are specialized proteins that specifically recognize and bind to one particular protein that specifically recognize and bind to one particular protein. Antibody production and binding to a foreign substance or antigen, often is critical as a means of signaling other cells to engulf, kill, or remove that substance from the body.

Antigens and chemokines can be selected based on their ability to attract and/or increase activation of T cells and NK cells, T cells and B cells, NK cells and B cells, or all three of T cells, NK cells, and B cells. DC or populations of DC can be engineered to, individually or pooled, express one or more than one exogenous chemokine that attracts or increases activation of $CD4^+/CD8^+$ T cells, NK cells, and/or B cells. DC can be engineered to express at least one exogenous chemokine selected from within the classes C, CC, CXC, and $CX_3C$ that attracts or increases activation of T cells, e.g., CCL-1, CCL-2, CCL-3, CCL-4, CCL-5, CCL-8, CCL-13, CCL-17, CCL-18, CCL-20, CCL-21, CXCL-9, CXCL-10, CXCL-11, CXCL-14, CXCL-16, and XCL1. DC can also be engineered to express at least one exogenous chemokine selected from within the classes C, CC, CXC, and $CX_3C$ that attracts or increases activation of NK cells, e.g., CCL-8 and CX3CL-1. DC can be engineered to express at least one exogenous chemokine selected from within the classes C, CC, CXC, and $CX_3C$ that attracts or increases activation of B cells, e.g., CCL-8, CCL-18, and CXCL-13. DC can also be engineered to express CCL-21, CX3CL-1, and CXCL-13 to attract or increase activation of T cells, NK cells, and B cells.

Selection of Optimized Immune Cell Subsets

It is known that distinct antigens elicit distinct patterns of immune cell involvement. As examples, some antigen(s) primarily trigger B cells to produce antibodies, some antigens primarily trigger CD4$^+$ T helper cells to become activated and secrete chemokines, some antigens primarily trigger CD8$^+$ T effector (or "killer") cells to lyse tumor cells (or virally infected normal cells), and so on. Different immune cell types are involved in the production of antibody by plasma cells, generation of cytotoxic T lymphocytes, generation of activated NK cells, induction of delayed type hypersensitivity reactions, and macrophage activation. Cooperation between the different cell types is desirable for optimal clearing of the antigen, including interactions between antigen-specific and non-specific effector cells. CD4$^+$ T cells play a central role in coordinating an antigen-specific immune response through cytokine release. Ultimately, non-specific phagocytic cells are responsible for clearing the antigen and macrophages and fibroblasts resolve any damage caused by the antigen and promote healing. Thus, the immune cell types most effective in eliminating an antigen may depend on the particular antigen. Thus, in some embodiments, the process can also include identifying a set of immune cell types that are intended to be recruited and/or activated by the injected end-product resulting in the formation of the functional bioengineered lymph node structure(s). Therefore, the methods can include a set of in vitro assays that measure, for each immune cell type, its response to the particular antigen-loaded chemokine-expressing DC (e.g., DC loaded with antigen from a specific patient, tumor type, or pathogen) and also whether the particular chemokine selected to recruit each immune cell type also enhances/activates that immune cell type's function/activity against the particular antigen. The immune cells used in these assays will generally be assayed and/or selected on the basis of their chemotaxis to certain chemokines. Those immune cell types, such as CD4$^+$ T cells, CD8$^+$ T cells, NK cells, and/or B cells, that are most effectively activated by the antigen and functionally enhanced by the chemokine are those which are desired to be recruited to the bioengineered lymph node structure at the site of injection and thus can be used to guide selection of chemokines to express in the DC.

These additional assays can employ distinct antigens to determine which chemokine-driven migrated immune cell type(s) displays strongest activation and function with each antigen chosen and loaded onto the DC (thus allowing for optimization). The chemokines and antigens most effective in attracting and/or activating the desired immune cell types are selected and the cDNAs of the selected chemokines of interest are then engineered into recombinant expression vectors (e.g., adenovirus) for introduction into TL-DC in vitro. Chemokine-secreting TL-DC are then injected into the skin of tumor-bearing humans or animals (again, similar to previous work with SLC/CCL-21) to determine the existence of created bioengineered lymph node structures, their cellular composition, and their antigen-specificity and functional activity. Effects on tumor growth in these recipients can be measured as well. The present methods are not limited to oncology as creation of functioning bioengineered lymph node structures could be expanded to other areas for boosting immunity against a variety of antigens (e.g., in infectious disease) or improving immune systems impaired by aging, toxins, or disease. Moreover, multiple bioengineered lymph node structures can be created, each being autonomous, in a single host, and each created bioengineered lymph node structure can have completely distinct cellular composition(s) and function(s) in a single host as well. Also, the methods are not limited to immune cells contained already in the host, as they can also include administration of treatments to increase resident immune cells, such as with bone marrow and peripheral blood stem cell transplantation and/or the adoptive transfer of large numbers of defined immune cell subpopulations (e.g., ex vivo produced NK cells or expanded tumor infiltrating lymphocytes or TcR gene-modified T cells) that could traffic and accumulate at the injection site of chemokine(s)-producing TL-DC, e.g., using methods known in the art (Mulé et al., Science 225:1487, 1984; Geraghty and Mulé, In: Gene Therapy in the Treatment of Cancer: Progress and Prospects. B. E. Huber and I. Magrath (eds.). Cambridge University Press, pp. 137-148, 1998).

Antigens

Antigens that can be loaded onto the chemokine-expressing DC include without limitation, tumor antigens, e.g., from solid tumors, liquid tumors, hematopoietic-derived tumors, autologous cancer cells, allogeneic cancer cell lines, or cancer cells comprising cells from two or more different cancer types or different cell lines; tumor antigen(s) can be in the form of a suspension of either lysed tumor cells, fragments of tumor cells, tumor cells that remain substantially intact following exposure to UV irradiation or gamma irradiation, known whole proteins, known peptides, cDNAs or mRNAs, or whole live or killed (necrotic or apoptotic) autologous or allogeneic tumor cells. Any method known in the art can be used for preparing dead tumor cells, so long as the dead tumor cells retain tumor-specific antigens, e.g., antigens expressed on the surface of the tumor cells. See, e.g., Chang et al., Clin Cancer Res 8:1021 (2002); Geiger et al., Cancer Res 61:8513 (2001). A number of tumor-associated antigens (TAA) are known in the art and can be loaded onto the chemokine-expressing DC. Methods for detecting TAAs are well known. For example, several TAAs over-expressed in NSCLC cell lines have been identified. These include MAGE-1, 2, and 3, CEA, HER-2/neu, and WT-1. Characterization of 31 NSCLC lines showed that the majority tested express HER-2/neu (90%) and CEA (58%) on the cell surface. Two lung adenocarcinoma cell lines, NCI-H1944 and NCI-H2122, that together express HER-2/neu, CEA, GD-2, WT-1, and MAGE-1, -2, and -3 (Wroblewski et al., Lung Cancer 33:181 (2001)) can be used.

Viral antigens can include, e.g., viral particles, viral proteins, or viral genetic material. Bacterial antigens can include, e.g., whole or intact killed bacteria, bacterial lipopolysaccharide, bacterial flagellin, lipoteichoic acid from Gram positive bacteria, or peptidoglycan. Fungal antigens can include, e.g., whole or intact killed fungi or gp43 glycoprotein (*Principles of Immunopharmacology*, Birkhäuser Basel, 2nd edition, 2005).

Subjects to be Treated

In one aspect of the methods described herein, the subject has, or is at risk of developing, cancer, or a viral, bacterial, or fungal infection. In some embodiments of the methods described herein, the subject has, or is at risk of developing, cancer, e.g., leukemia, lymphoma, multiple myeloma, lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer. A subject that "has, or is at risk of developing, cancer" is one having one or more symptoms of and/or known risk factors for, cancer, as identified by a health care provider. Symptoms of cancer vary greatly and are well-known to those of skill in the art and include, without limitation, breast lumps, nipple changes, breast pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, or pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, pancreas metastases, difficulty swallowing, and the like. A subject that is "at risk of developing cancer" is one that has a predisposition to develop cancer (i.e., a genetic predisposition develop cancer such as a mutation in a tumor suppressor gene, e.g., BRCA1, p53, RB, or APC) or has been exposed to conditions that can result in cancer. Thus, a subject that is "at risk of developing cancer" can be one that has been exposed to mutagenic or carcinogenic levels of certain compounds (e.g., carcinogenic compounds in cigarette smoke such as acrolein, arsenic, benzene, benz{a}anthracene, benzo{a}pyrene, polonium-210 (Radon), urethane, or vinyl chloride). Moreover, the subject can be "at risk of developing cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T cell leukemia-lymphoma virus. A health care provider can identify a subject who is at risk of developing cancer based on the above factors and/or the general knowledge in the art.

In some embodiments of the methods described herein, the subject has, or is at risk of developing, a viral infection, e.g., influenza virus, rhinovirus, varicella zoster virus, human immunodeficiency virus, human papillomavirus, herpes simplex virus, hepatitis A/B/C/D/E/F/G virus, hemorrhagic fever virus, Coronavirus, SARS virus, smallpox virus, vaccinia virus, variola virus, West Nile virus, Ebola virus, cowpox virus, monkeypox virus, or simian immunodeficiency virus. A subject that "has, or is at risk of developing, a viral infection" is one having one or more symptoms of the condition. Symptoms of a viral infection vary greatly and are known to those of skill in the art and include, without limitation, malaise, fever, chills, decreased appetite, dehydration, headaches, tachypnoea, hypoxemia, and diaphoresis. Common viral infections may be diagnosed based on symptoms. Blood may be tested for antibodies to viruses or for antigens. Polymerase chain reaction (PCR) techniques may be used to make many copies of the viral genetic material, enabling doctors to rapidly and accurately identify the virus. A subject that is "at risk of developing a viral infection" is one that has been exposed to conditions that can result in a viral infection or is immunocompromised. An immunocompromised subject may be particularly vulnerable to opportunistic infections, in addition to infections that affect subjects with normal immune systems.

In one aspect of the methods described herein, the subject has, or is at risk of developing, a bacterial infection, e.g., *Bacillus anthracis, Bacillus subtilis, Bordetella pertussis, Campylobacter jejuni, Campylobacter pylori, Chlamydia trachomatis, Clostridium botulinum, Clostridium difficile, Clostridium perfringens, Clostridium tetani, Corynebacterium diphtheriae, Corynebacterium fusiforme, Enterococcus faecalis*, enteropathogenic *Escherichia coli, Haemophilus influenzae, Helicobacter pylori, Klebsiella pneumoniae, Listeria monocytogenes, Mycobacterium tuberculosis, Neisseria gonorrhoeae, Pseudomonas aeruginosa, Rickettsia rickettsii, Salmonella typhimurium, Shigella dysenteriae, Staphylococcus aureus, Streptococcus faecalis, Streptococcus pneumoniae, Streptococcus pyogenes, Vibrio cholerae*, or *Yersinia pestis*. A subject that "has, or is at risk of developing, a bacterial infection" is one having one or more symptoms of the condition. Symptoms of a bacterial infection vary greatly and are known to those of skill in the art and include, without limitation, malaise, fever, chills, decreased appetite, dehydration, headaches, tachypnoea, hypoxemia, and diaphoresis. A bacterial infection can be diagnosed by culturing a sample (e.g., blood or urine) to determine the bacterial species present in the sample. A subject that is "at risk of developing a bacterial infection" is one that has an open wound or is immunocompromised. An immunocompromised subject may be particularly vulnerable to opportunistic infections, in addition to infections that affect subjects with normal immune systems.

In some embodiments of the methods described herein, the subject has, or is at risk of developing, a fungal infection, e.g., *Candida albicans, Candida glabrata, Candida parapsilosis, Candida utilis, Aspergillus fumigatus, Aspergillus flavus, Cryptococcus neoformans, Histoplasma capsulatum, Pneumocystis jirovecii*, or *Stachybotrys chartarum*. A subject that "has, or is at risk of developing, a fungal infection" is one having one or more symptoms of the condition. Symptoms of a fungal infection vary greatly and are known to those of skill in the art and include, without limitation, fever, cough, chest pain, severe headaches, and breathlessness. A fungal infection can be diagnosed by culturing a sample (e.g., blood or urine) to determine the fungal species present in the sample. A subject that is "at risk of developing a fungal infection" is one that has an open wound or is immunocompromised. An immunocompromised subject may be particularly vulnerable to opportunistic infections, in addition to infections that affect subjects with normal immune systems.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

An "effective amount" is an amount sufficient to effect beneficial or desired results. For example, a therapeutic amount is one that achieves the desired therapeutic effect, i.e., a reduction in fibrosis. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

EXAMPLES

The invention is further described in the following examples, which do not limit the scope of the invention described in the claims.

Example 1

RANTES/CCL-5 Expressing Tumor Cells Can Prevent Tumor Growth

Weakly-immunogenic sarcoma cells (denoted WP4; Mulé et al., Hum Gene Ther. 7(13):1545-53, 1996.) were gene-modified (by plasmid transfection) to secrete high levels of RANTES/CCL-5. RANTES/CCL-5 potently attracts CD8+ tumor infiltrating lymphocytes (TIL) in vitro (Mulé et al., Hum Gene Ther. 7(13):1545-53, 1996.). Of importance, the capacity of RANTES/CCL-5-secreting tumor cells to form solid tumor masses was tested in recipient mice. Ten million cells from each of two RANTES/CCL-5-secreting cultures (WP4-1, WP4-12), non-secreting tumors (WP4-2, WP4-3), or a transfection control (WP4-NEO) were injected s.c. into recipient mice and the incidence of tumor formation in each group was followed over time. In every case, mice injected with the RANTES/CCL-5-secreting tumor cells failed to develop solid tumor masses out to day 51 whereas all other mice developed large tumor masses (Table 1). mAb depletion experiments demonstrated that CD4+ T cells (partially), CD8+ T cells, and macrophages were responsible for the antitumor effect elicited in vivo by RANTES/CCL-5. However, RANTES/CCL-5 was not highly therapeutic in the setting of either an already established WP4 tumor or in the prevention of a poorly-immunogenic tumor (i.e., B16 melanoma).

TABLE 1

RANTES-Secreting MCA-205 (WP4) Tumors Fail to Grow Progressively

| Tumor transfectants[a] | RANTES-secreting | Tumor Incidence Day 21 | Tumor Incidence Day 51 |
|---|---|---|---|
| WP4-1 | + | 0/6[b] (0 ± 0)[c] | 0/6 (0 ± 0) |
| WP4-2 | − | 6/6 (9 ± 1) | 6/6 (16 ± 2) |
| WP4-3 | − | 6/6 (7 ± 1) | 6/6 (11 ± 1) |
| WP4-12 | + | 0/6 (0 ± 0) | 0/6 (0 ± 0) |
| WP4-NEO | − | 6/6 (8 ± 1) | 6/6 (14 ± 1) |

[a]Injected s.c. at 1 × 10$^7$ cells/site
[b]Number with tumor/total
[c]Mean tumor diameter (mm ± SEM)

Example 2

SLC/CCL-21 Expressing DC have Enhanced CD4+/CD8+ Chemoattraction In Vitro

Based on the knowledge that SLC/CCL-21 is chemoattractive to naïve CD4+ T cells, naïve CD8+ T cells, and dendritic cells in vitro (Saeki et al., J. Immunol. 162:2472-2475, 1999; Yoshida et al., J. Biol. Chem. 273:7118-7122, 1998; Kellermann et al., J. Immunol. 162:3859-3864, 1999; Gunn et al., Proc. Natl. Acad. Sci. USA, 95:258-263, 1998), experiments were conducted to test the capacity of SLC/CCL-21 gene-modified DC (by adenovirus transduction) to enhance the efficacy of DC-based tumor vaccines utilizing a series of murine tumor models (described in Kirk et al., Cancer Res. 61(5):2062-70, 2001.; Kirk et al., Cancer Res. 61(24):8794-802, 2001.). To that end, an adenoviral vector containing the gene for SLC/CCL-21 was constructed. A microchemotaxis assay was used to determine the levels of SLC/CCL-21 produced in the supernatant by gene-modified DC. Supernatants from infected cells were used as a source of chemoattractant in microchemotaxis assays with splenic responder cells. Microchemotaxis was performed using a range (10-5,000 ng/ml) of concentrations of recombinant SLC/CCL-21 to generate a standard curve for T cell chemotaxis. From the standard curve, it is possible to determine the concentration of chemokine present in DC-cultured supernatants. The standard curve used in determining SLC/CCL-21 concentrations was generated by analyzing the migration of CD41+ cells in the splenocyte responders. Similar values were obtained using a standard curve generated from migrating CD81+ cells or by total migrating lymphocytes. As shown in FIG. 1, which represents the data from nine separate experiments, ~750 ng of SLC/CCL-21 were produced within 18 hours by 1×10$^6$ SLC/CCL-21 gene-modified DC. SLC/CCL-21 was detected in 24-hour culture supernatants 3 days after infection, suggesting that gene expression endured for at least this period of time. The amount of chemotactic activity in cultured supernatants from SLC/CCL-21 gene-modified DC was >10 fold more than that elicited by GFP-expressing DC (FIG. 1).

Generation of Adenoviral Vectors

Adenoviruses containing each chemokine cDNA are constructed using AdEasy XL adenoviral vector systems (Stratagene, La Jolla, Calif.). Each chemokine gene is obtained by digestion of pcDNA/chemokine gene with HindIII and EcoRV. A1148 chemokine expression plasmids are a gift from Dr. Thomas Schall. The cDNA fragment is inserted into the HindIII and EcoRV sites of the pShuttle-CMV transfer vector. Presence of the insert is confirmed by restriction analysis and DNA sequence analysis. The transfer vector is linearized with PmeI, treated with alkaline phosphatase, then isolated by gel purification. The linearized transfer vector and pAd-Easy-1 vector are co-transformed into BJ5183AD bacteria by electroporation. In the bacteria, homologous recombination occurs to give rise to a full-length recombinant adenovirus lacking the Ad5 E1 and E3 genes. Transformants are incubated for 1 hour at 37° C., then plated on a LB-kanamycin plate. Plates are incubated overnight. Plasmid DNA is purified from distinct colonies and digested with PacI to identify clones with the correct size. Recombinant clones are characterized by DNA sequencing to verify the orientation of the cDNA prior to further amplification. High-titer adenovirus is prepared in 293A cells using the ViraPack Transfection kit (Stratagene). Virus is concentrated using CsCl banding. Viral concentration is determined by soft agar cultures. Aliquots of adenoviruses are maintained at −80° C. until immediately prior to use.

Murine DC Production

Bone marrow cells (BMC) are flushed from the femurs and tibias of B6 mice under aseptic condition. Erythrocytes are lysed with ACK lysing buffer (0.15 M NH$_4$Cl, 1 mM KHCO$_3$, and 0.1 mM EDTA in sterile water). Erythrocyte-depleted BMC are washed twice with Dulbecco's PBS (Mediatech, Inc.) and suspended in complete medium (CM) containing 20 ng/ml of mouse GM-CSF and 10 ng/ml of mouse IL-4 (both from R&D Systems, Minneapolis, Minn.) at the concentration 1×10$^6$ cells/ml, and incubated at 37° C., 5% CO$_2$. On day 5, non-adherent cells are collected and DC are highly enriched (>95%) by density centrifugation over OptiPrep (Axis-Shield PoC AS, Oslo, Norway).

Genetic Modification of DC with Adenoviral Vectors

DC are resuspended at a concentration of 1×10$^7$ cells/ml in RPMI 1640+2% FCS and placed in a 15-ml conical tube. Virus is added (generally at a ratio of 16,048 vector particles per DC), the suspension is mixed well, and the tube is incubated at 37° C. for 2-4 hours. Nine volumes of CM with 20 ng/ml GM-CSF and 10 ng/ml IL-4 are added, and the cells are transferred to tissue culture dishes. Cells are incubated for 18 hours at 37° C., supernatants recovered, and the cells purified by incubation in PBS with 3 mM EDTA and gentle scraping. Using an adenovirus encoding GFP, a transfection efficiency of >75% is usually achieved. In some cases, the cells are cultured for 72 hours with supernatant harvested every 24 hours. The cells are washed several times in PBS, and resuspended to $5 \times 10^6$ cells/ml.

Purification of Murine Immune Cell Subsets

Magnetic beads for cell separations are purchased as kits from Miltenyi Biotec (Auburn, Calif.) and Invitrogen (Carlsbad, Calif.). $CD4^+$ or $CD8^+$ T cell subsets are purified from the spleens and lymph nodes of mice bearing 10-day B16 melanoma using $CD4^+$ or $CD8^+$ T cell Isolation Kit, respectively. $CD4^+CD25^+$ T regulatory cells are purified from the spleens of these mice using the $CD4^+CD25^+$ Regulatory T cell Isolation Kit (Invitrogen). NK cells are purified untouched from the spleens of these mice using the NK cell Isolation Kit (Miltenyi Biotec). B cells are purified untouched from spleens and lymph nodes of these mice using the B cell Isolation Kit (Miltenyi Biotec). Cell separations are performed on an autoMACS Separator system (Miltenyi Biotec).

Microchemotaxis

Splenocyte responder cells were generated by gently rubbing spleens between frosted glass slides and passing over a nylon mesh filter (70 mm) Red blood cells were lysed, and the splenocytes were resuspended in RPMI 1640 medium containing 5% FCS(RPMI-FCS) and subjected to two rounds of adherence to plastic at 37° C. Nonadherent cells were resuspended to $1 \times 10^7$ cells/ml in RPMI-FCS prior to use in microchemotaxis assays. DC responders were obtained from 7-day bone marrow cultures as described above and were used at $2.5 \times 10^6$ cells/ml in RPMI-FCS. Assays were performed in 24-well plate format with 6.5-mm diameter, 5 mm pore polycarbonate Transwell insets (Costar, Cambridge, Mass.) in duplicate samples. SLC/CCL-21 was added to the lower chambers at the indicated concentrations in a volume of 600 ml and incubated at 37° C. for 30 min prior to addition of cells. One hundred ml of cell suspension were added to the top chamber, and the assay was carried out at 37° C. in a humidified incubator with 5% $CO_2$. A 1:5 dilution of the cells was also directly added to the lower chamber of two wells for determination of the input amount. After 2 hours, the assay was stopped by the removal of the inserts, followed by the addition of $10^4$ polystyrene beads (15-mm diameter; Bangs Laboratories, Fishers, Ind.) to the lower chamber. Samples were stained with antibodies against CD4 and CD8 (splenocytes) or MHC II and CD86 (DC) and counted on a FACScaliber (Becton Dickinson, San Jose, Calif.). In separate experiments, CD4 and CD8 cells were counterstained for expression of CD62L (all antibodies from PharMingen, San Diego, Calif.). The number of cells in each sample (and the input) was determined by the equation: (number of cell events/number of bead events)$\times 10^4$ beads/sample. The percentage of migration in each sample (% input) was determined by the equation: [number of cells in sample/(number of cells in input$\times$5)]$\times$100.

Example 3

SLC/CCl-21 Expressing TL-DC have Enhanced Antitumor Activity In Vivo

Figure 2:
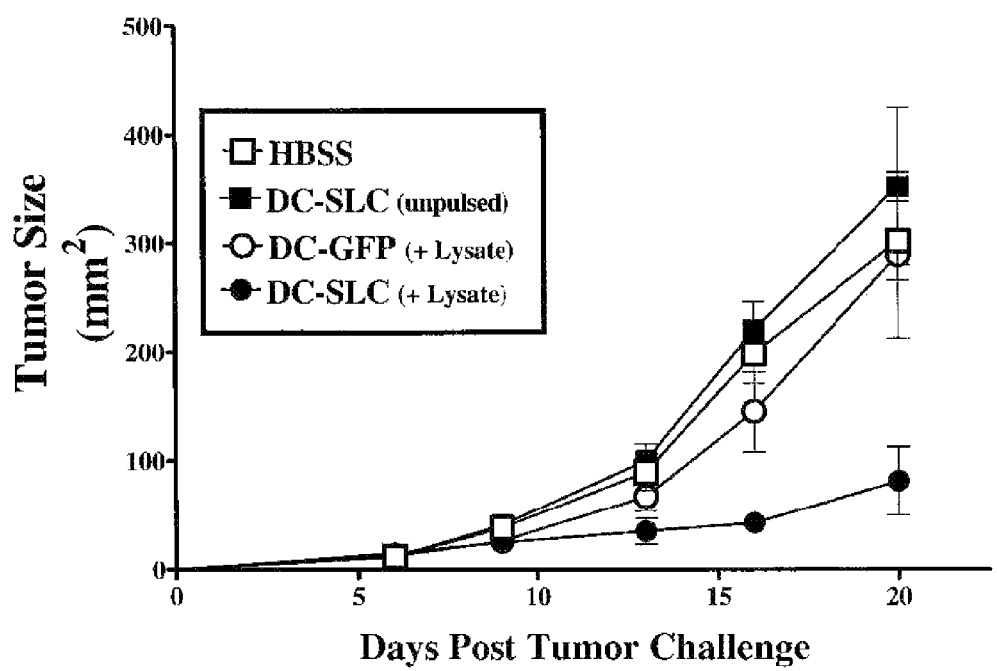
FIG. 2 is a line graph showing the size of tumors in mice immunized with DC expressing SLC/CCL-21 (or GFP) pulsed with B16-BL6 tumor lysate. Mice bearing 6-day subcutaneous (s.c.) B16-BL6 tumors in the right flank were immunized in the left flank twice on days 6 and 13 with $5\times10^5$ DC that had been infected with adenovirus encoding SLC/CCL-21 (●) or GFP (○) and pulsed for 18 hours with B16 cell lysate. Control mice received injections of saline (HBSS) alone (□). Tumor size was measured. Bars, SE.

Established B16-BL6 tumors were treated with tumor lysate-pulsed DC (TL-DC) to determine whether treatment could be improved by genetically modifying the DC to express SLC/CCL-21. Pulsing of DC with tumor lysate did not significantly affect the levels of SLC/CCL-21 produced by gene-modified DC. Mice bearing 6-day established tumors were immunized with DC expressing SLC/CCL-21 (or GFP) and pulsed with B16-BL6 tumor lysate contralaterally to the site of growing tumors. FIG. 2 shows that although GFP gene-modified DC were ineffective in reducing the growth of s.c. tumors, SLC/CCL-21-expressing DC were able to mediate a significant antitumor response. This response was dependent upon presentation of tumor antigen(s) by the DC, because unpulsed SLC/CCL-21 gene-modified DC were unable to elicit an antitumor response when administered at a site distal from the tumor (FIG. 2).

Figure 3:
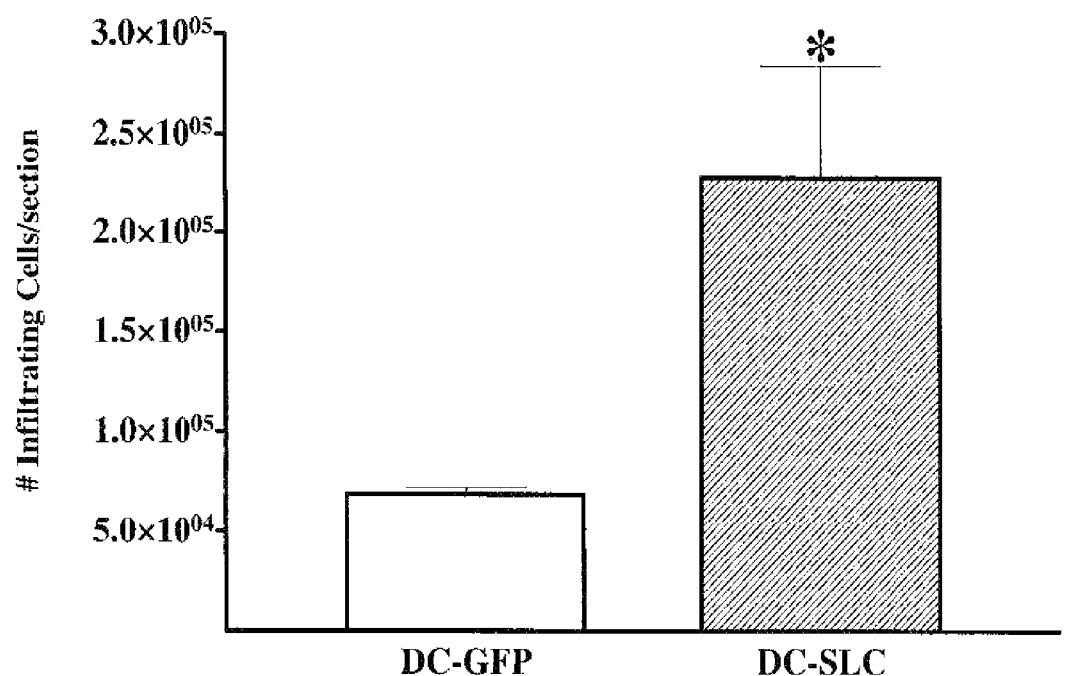
FIG. 3 is a bar graph showing the mean numbers of CD4$^+$ and CD8$^+$ T cells that migrate to the injection sites containing SLC/CCL-21-expressing DC. Mice received injections s.c. with $1\times10^6$ tumor lysate-pulsed DC expressing either GFP (□) or SLC/CCL-21 (■). Three days after injection, 1.5×1.5-cm sections of skin were harvested, minced, and digested in collagenase, DNase I, and hyaluronidase to obtain a single cell suspension (approximately $1\times10^6$ cells/ml). Polystyrene beads ($C_f=5\times10^5$ beads/ml) were added to enumerate migrating T cells. T cell subsets were analyzed by FACS. Data are presented as the mean numbers of migrating cells from four (GFP) and five (SLC/CCL-21) mice; bars, SE. *, p<0.05 by Student's t test.

One possible explanation for the enhanced effect of SLC/CCL-21 gene modification on TL-DC immunizations is enhanced recruitment of host-derived T cells in vivo. Because the vast majority of DC remain at the s.c. immunization site 24 hours after injection (Morse et al., Cancer Res. 59(1):56-8, 1999.; Eggert et al., Cancer Res. 59(14):3340-5, 1999.), it is possible that T cells would migrate to skin sites containing SLC/CCL-21-expressing DC. To determine the influx of T cells into DC skin injection sites, mice were immunized s.c. with B16-BL6 TL-DC expressing either GFP or SLC/CCL-21 and skin samples were harvested 3 days later. After enzymatic disaggregation, these samples were analyzed for the presence of CD41 and CD81 cells by FACS. As shown in FIG. 3, SLC/CCL-21-expressing DC attracted>2-3-fold more $CD4^+$ and $CD8^+$ T cells to the injection site (p<0.05). These data suggested that the improved adjuvanticity of DC resulting from expression of SLC/CCL-21 may be attributable, in part, to increased migration of T cells to the site of immunization.

Figure 4:
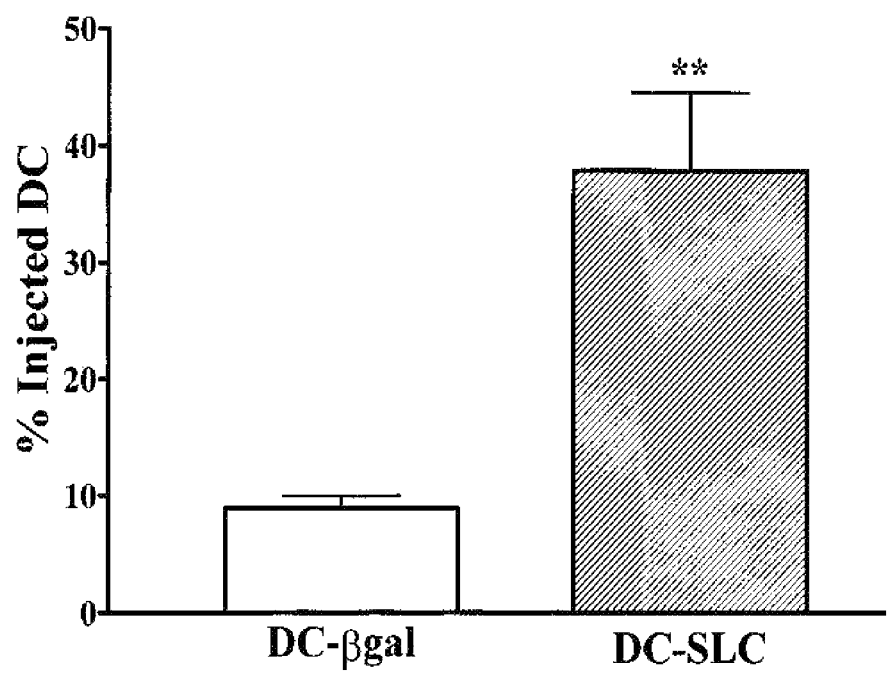
FIG. 4 is a bar graph showing the retention of gene-modified DC in treated tumors. Mice bearing 6-day s.c. B16 tumors were injected with $1\times10^6$ genetically modified DC that were labeled with PKH26 dye prior to injection. Tumors were harvested 24 hours after injection, stained with FITC-conjugated anti-CD11c, and analyzed for the presence of labeled cells by flow cytometry. Cell percentages were quantified. Bars, SE.

DC genetically modified to express SLC/CCL-21 (denoted DC-SLC/CCL-21) or the control protein β-galactosidase (denoted control DC) were labeled with the dye PKH-26 (567-nm emission) prior to injection into s.c. B16 melanoma to follow the migration of these gene-modified DC. Tumors and draining lymph nodes (DLN) were harvested 24 hours after injection and analyzed for the presence of labeled cells. In tumors injected with DC-SLC/CCL-21, 40% of injected cells remained in the tumor one day later, significantly more than labeled control DC (FIG. 4). It is unlikely that the PKH-26$^+$ cells represented uptake of dye or labeled DC by tumor cells or resident macrophages, because the dye-containing cells expressed the DC marker CD11c. Furthermore, these values may be underestimates because of the likelihood that the recovery process is not able to fully retrieve all viable DC within the tumor digest. The increased retention of the SLC/CCL-21 gene-modified DC was likely the result of both improved cell viability (the anti-apoptotic effect of SLC/CCL-21) and the expression of SLC/CCL-21 by the DC as SLC/CCL-21 expressing DC retained their ability to migrate along a SLC/CCL-21 gradient in vitro.

Figure 5:
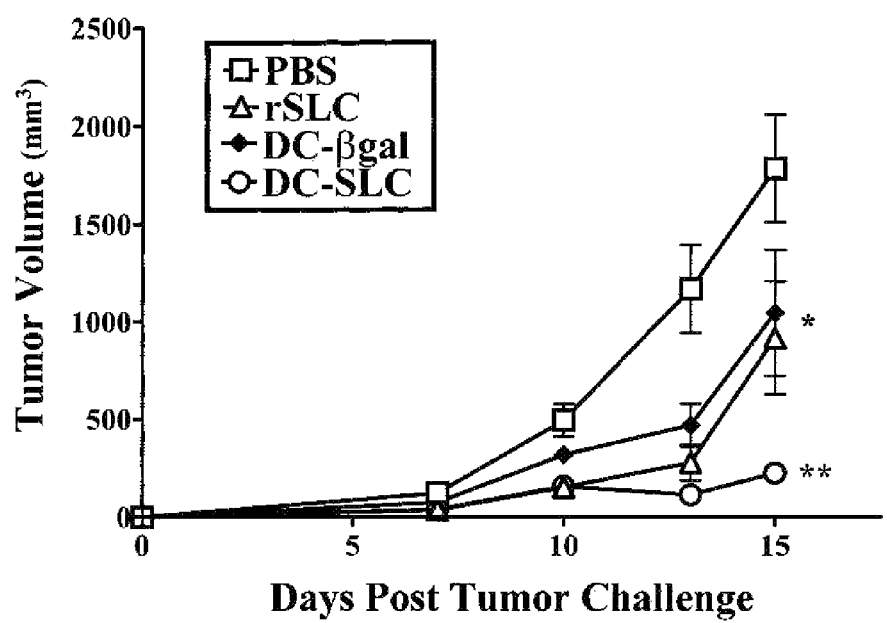
FIG. 5 is a line graph showing the volume of a tumor after treatment of established B16 melanoma with recombinant (r)SLC/CCL-21 and gene-modified DC. Tumors were established in B6 mice by s.c. injection with $1\times10^5$ viable cells. Six days after tumor challenge, mice were treated with daily injections of rSLC/CCL-21 (3 μg/dose) from days 6-10 or $1\times10^6$ gene-modified DC on days 6 and 9. Tumors were monitored for growth by perpendicular diameter measurement. Tumor volumes (means; bars, SE) are presented in mm$^3$*, p<0.05 for DC-βgal and rSLC/CCL-21 versus PBS; **, p<0.01 for DC-SLC/CCL-21 versus all other groups. n=6-10 mice/time point.

Because DC-SLC/CCL-21 remained in the tumor site after intratumoral administration without subsequent migration to the DLN, the antitumor effect elicited at the tumor site by these genetically modified APC was further investigated. Mice bearing s.c. B16 melanoma were treated with intratumoral injections of DC-SLC/CCL-21 or control DC on days 6 and 9. The SLC/CCL-21 production by gene-modified DC was 517.4±59.13 ng/$1 \times 10^6$ cells/18 hours, as measured by a microchemotaxis-based bioassay. Mice treated intratumorally with either control DC or recombinant (r)SLC/CCL-21 (3 μg daily from days 6 to 10) experienced a modest inhibition of tumor growth over the course of study (FIG. 5). In contrast, mice treated with DC-SLC/CCL-21 demonstrated marked tumor growth inhibition, which was significantly greater than either control DC or rSLC/CCL-21 (FIG. 5). Tumor growth inhibition by DC-SLC/CCL-21 was evident for at least 28 days after tumor challenge, at which time all mice were sacrificed because of excessively large tumors in the control groups.

Tumor Loading of Gene-Modified DC

After adenovirus infection, DC are resuspended to $1\times10^6$ cells/ml in CM containing lysate from B16 melanoma cells that have been lysed by three rapid freeze/thaw cycles and spun at ~100×g to remove cellular debris. The DC are pulsed at a 3:1 tumor cell:DC ratio for 18 hours. After pulsing, the TL-DC are collected, their cultured supernatants are harvested for microchemotaxis assay or ELISA, and washed several times in PBS prior to use.

Example 4

TL-DC-SLC/CCL-21 Enhance T Cell Activation In Vivo

Figures 6A, 6B:
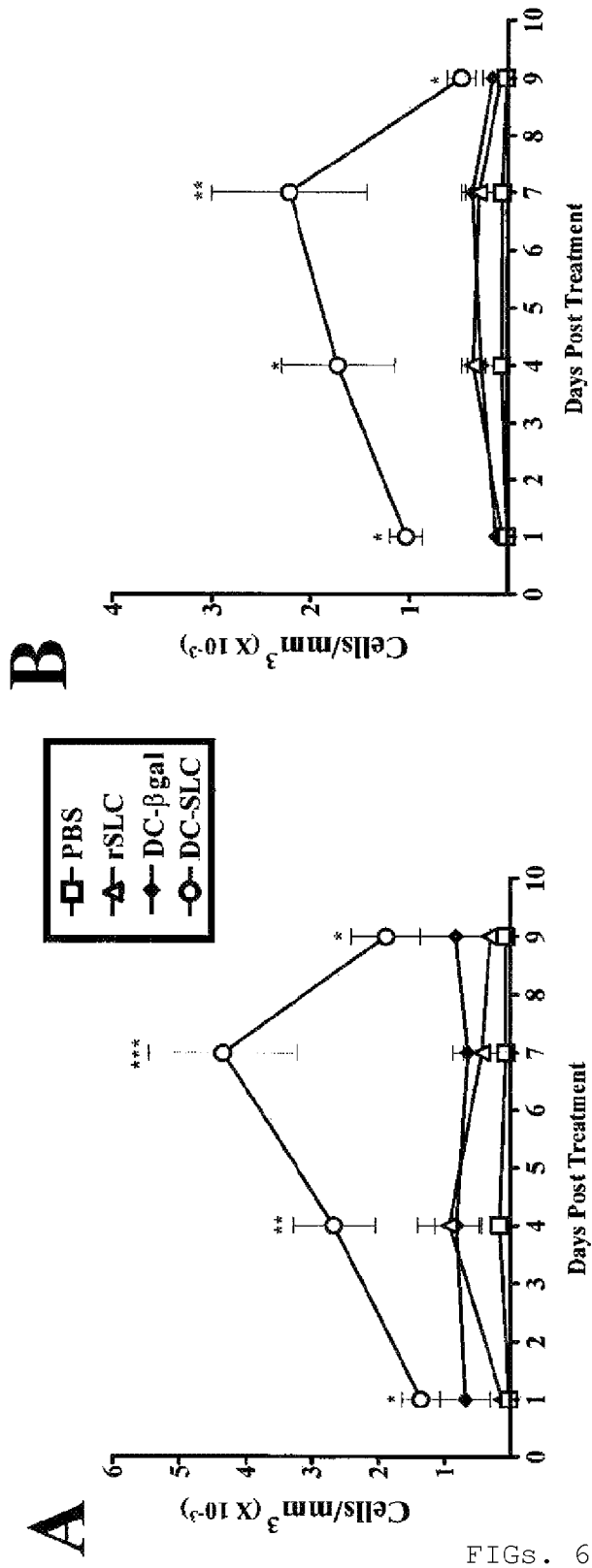
FIGS. 6A and 6B are line graphs depicting the numbers of recently activated T cells within treated tumors. Tumors were enzymatically digested and analyzed for presence of CD25 in the CD4$^+$ (FIG. 6A) and CD8$^+$ (FIG. 6B) T cell subsets with PE-conjugated anti-CD25- and Cy-Chrome-conjugated antibodies. Analysis was carried out in the CD11b-/B220-population, and cell numbers were normalized to the tumor volume. *, , and *, at least p<0.05, p<0.01, and p<0.001 for DC-SLC/CCL-21 versus all others groups, respectively. n=4-6 mice/time points; bars, SE.

Infiltrating T cells were analyzed for expression of CD25, which is known to appear within 24 hours of T cell activation. DC-SLC/CCL-21-treated tumors contained significantly more "early" activated CD4$^+$ and CD8$^+$ T cells as determined by expression of CD25 (FIG. 6). Expression of CD25 was found on ~30% of the CD4$^+$ and CD8$^+$ T cells in tumors treated with DC-SLC/CCL-21 24 hours after the first injection of DC and remained at this level until the last time point analyzed (FIG. 6). In the mice receiving control DC, rSLC/CCL-21, or saline, CD25 expression was also seen on ~30% of T cells 24 hours after the first injection but had dropped to <15% of CD4$^+$ and <10% of CD8$^+$ T cells 3 days later. Furthermore, there was no significant increase in the number of activated CD4$^+$ or CD8$^+$ T cells in tumors of control DC- or rSLC/CCL-21-treated mice at the 24 hour time point (FIG. 6). The decline in the relative expression of CD25 on T cells in the control DC-treated tumors was paralleled by an increase in the absolute number of activated T cells found in the DLN of these animals.

Example 5

TL-DC-SLC/CCL-21 Enhance Accumulation of IFN-γ$^+$ Effector Cells In Vivo

Figure 7A:
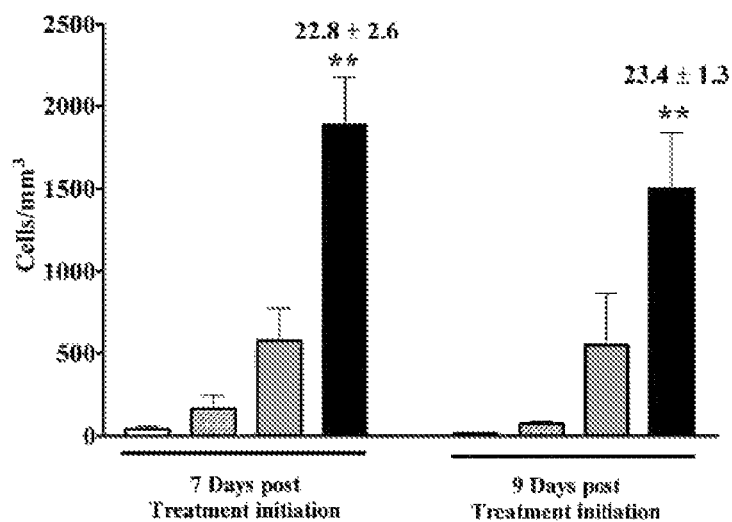
FIGS. 7A and 7B are bar graphs depicting the numbers of IFN-γ-producing T cells within treated tumors. Intracellular IFN-γ cytokine staining in the CD4$^+$ (FIG. 7A) and CD8$^+$ (FIG. 7B) subsets was performed on tumor samples. Cell numbers were normalized to tumor volume and presented as cells/mm$^3$ and *, at least p<0.01 and p<0.001 for DC-SLC/CCL-21 versus all other groups, respectively. n=4 mice/time point. Numbers above columns for DC-SLC/CCL-21 represent the percentage (bars, SE) of CD4$^+$ (FIG. 7A) or CD8$^+$ (FIG. 7B) cells producing IFN-γ.
Figure 7B:
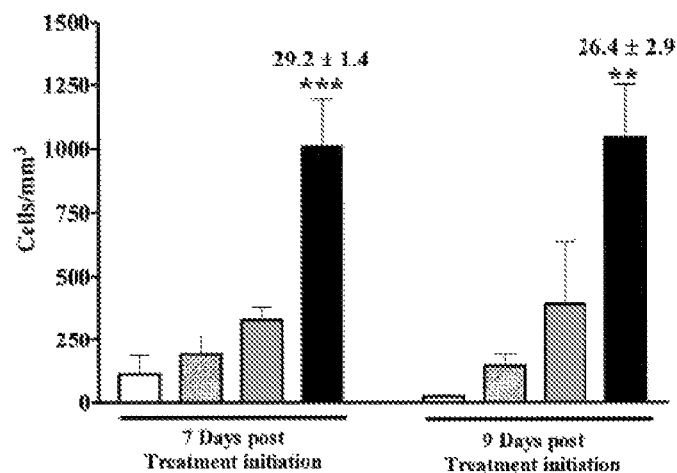

Tumor-infiltrating lymphocytes were also analyzed for the production of IFN-γ. To enumerate the number of effector T cells infiltrating the tumor, the production of IFN-γ was assayed by flow cytometry. Tumors isolated 7 and 9 days after the first injection of DC were stained for the presence of intracellular IFN-γ in CD4$^+$ and CD8$^+$ T cells after stimulation with PMA and ionomycin for 5 hours. In T cells isolated from DC-SLC/CCL-21-treated tumors, IFN-γ was expressed by ~25% of CD4$^+$ T cells and ~30% of CD8$^+$ cells. As no IFN-γ-producing CD4$^+$ and CD8$^+$ T cells were detected in LNs of naïve animals upon stimulation with PMA and ionomycin, the cytokine-producing T cells within the tumor represented effector cells and not naïve cells. In tumors treated with DC-CCL-21, the relative concentration of IFN-γ-producing cells was 3-5-fold higher than in control DC treated tumors and up to 50-fold higher than in saline-treated tumors (FIGS. 7A and 7B). There was not a significant increase in the number of IFN-γ-secreting T cells in mice treated with either control DC or rSLC/CCL-21. Taken together, these data demonstrate that treatment of tumors with DC-SLC/CCL-21 results in the accumulation of activated, IFN-γ-producing effector cells at the tumor site.

Intracellular Cytokine Staining

Tumors and the bioengineered lymph node structure are harvested from mice at various time points (generally at days 7 and 9; Kirk et al., Cancer Res. 61(5):2062-70, 2001.; Kirk et al., Cancer Res. 61(24):8794-802, 2001.) after treatment initiation and enzymatically digested as described above. Samples are resuspended in CM to $1-5\times10^6$ cells/ml and stimulated with PMA (50 ng/ml) and ionomycin (500 ng/ml; both from Sigma Chemical Co.) for 5 hours at 37° C. Brefeldin A (10 µg/ml; Sigma Chemical Co.) or monensin (3 µM; Sigma Chemical Co.) is added for the last 3 hours. To control for the possibility of any nonspecific mitogenic stimulus, LN cells from naïve mice are stimulated as above for comparison. Samples are washed once in HBSS and resuspended in PBS+ 1% FBS to $~1\times10^6$ cells/ml; polystyrene beads are added to a final concentration of $5\times10^5$ cells/ml. Samples are stained with FITC-conjugated antibodies to CD11b and B220 and Cy-Chrome-conjugated antibodies to CD4 or CD8. Samples are washed twice in PBS+1% FBS and fixed in PBS containing 4% paraformaldehyde and 0.5% saponin (Sigma Chemical Co.) for 30 minutes at room temperature. Samples are washed twice in PBS+1% FBS containing 0.5% saponin (permeabilization buffer) and stained with PE-conjugated antibodies to IFN-γ or IL-4 (or isotype control) for 30 minutes at 4° C. Cells are washed three times in permeabilization buffer and resuspended in ice-cold PBS prior to analysis by flow cytometry. Cells are analyzed for the presence of IFN-γ or IL-4 in the CD11b-/B220-fraction of lymphocyte gated events. Cell numbers are calculated as described above.

Example 6

TL-DC-SLC/CCL-21 can Prime T Cells In Vivo in the Absence of Endogenous Host Lymph Nodes To determine the specific location where the infiltrating T cells are primed, s.c. B16 melanoma was established in both conventional B6 mice and those deficient in lymphotoxin (LT)α (Ltα-/-). Ltα-/- mice lack all peripheral LNs and display an altered splenic architecture; however, these mice retain normal levels of circulating T lymphocytes (De Togni et al., Science 264:703-707, 1994). Tumor-bearing animals were treated with gene-modified DC on days 6 and 9, and tumors were harvested 24 hours and 7 days after the initiation of treatment. As with B6 mice, treatment of tumors in Ltα-/- mice with DC-SLC/CCL-21 resulted in an influx of both CD4$^+$ and CD8$^+$ T cells within 24 hours. Furthermore, CD25 was expressed at similar levels of tumor-infiltrating CD4$^+$ T cells in DC-SLC/CCL-21-treated tumors of Ltα-/- and B6 mice (17.8%±1.7 and 16.6%±1.9 for B6 mice and Ltα-/- mice, respectively).

Figure 8A:
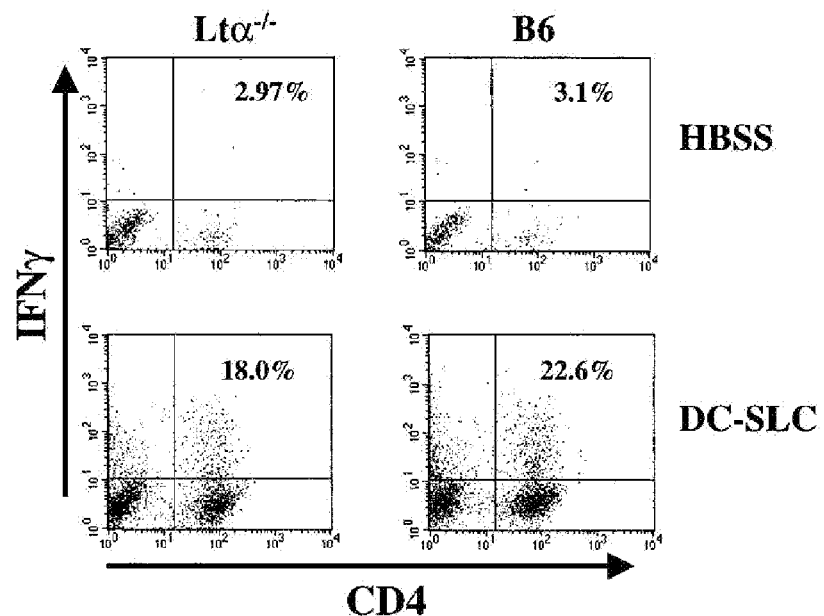
FIGS. 8A and 8B are scatter plots showing the priming and differentiation of effector T cells within treated tumors in the absence of lymph nodes (LN). B16 tumors were established in either B6 or Ltα$^{-/-}$ mice after injection of $1\times10^5$ tumor cells. Gene-modified DC were given on days 6 and 9, and tumors were harvested on day 14 after tumor challenge. Intracellular staining in IFN-γ was performed for CD4$^+$ (FIG. 8A) and CD8$^+$ (FIG. 8B) T cells. The numbers in the upper right-hand quadrant of each dot plot represent the average percentage of T cells producing IFN-γ (n=3 mice).
Figure 8B:
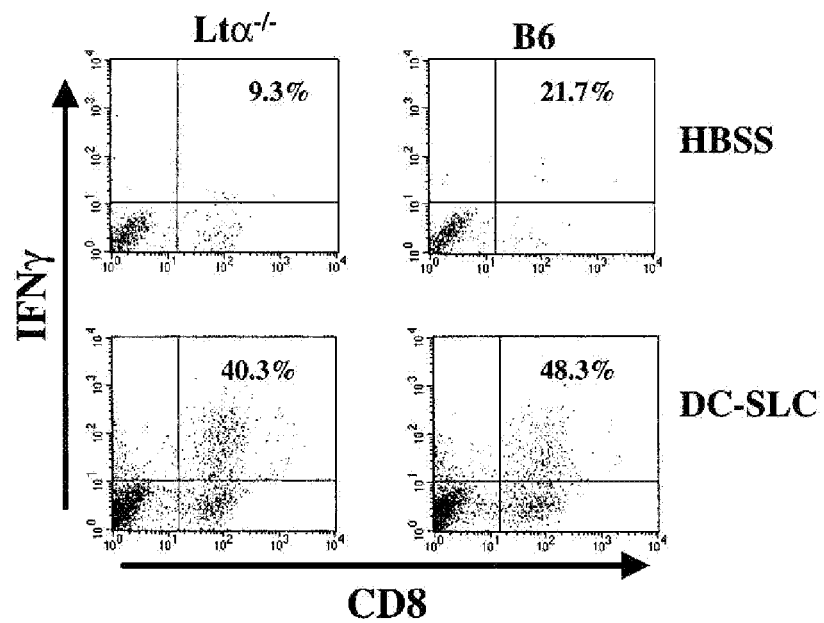

Tumors were also analyzed 7 days after the first treatment with gene-modified DC to detect the presence of cytokine-secreting effector cells. Treatment of s.c. tumors in Ltα-/- animals resulted in the expression of IFN-γ by both CD4$^+$ and CD8$^+$ T cells (FIGS. 8A and 8B). In B6 mice, 22.6%±0.7 of CD4$^+$ cells and 48.3%±11.1 of CD8$^+$ cells expressed IFN-γ. Of interest, similar percentages of T cells expressing this cytokine were also detected in DC-SLC/CCL-21-treated tumors of Ltα-/- mice (18.0%±1.5 and 40.3%±3.3 of CD4$^+$ and CD8$^+$ T cells, respectively). Furthermore, DC-SLC/CCL-21-treated tumors in the LTα gene knockout animals had a significant increase in the numbers of T cells present in the tumor at this time point (versus saline). Although, IFN-γ-producing cells were observed in tumors from saline (HBSS)-treated mice (FIGS. 8A and 8B), the small number of total T cells detected in these tumors likely renders the enumeration of cytokine production inaccurate. Of particular note, DC-SLC/CCL-21 treatment resulted in a significant inhibition of tumor growth in the Ltα−/− mice that was comparable with conventional B6 mice. At 14 days after tumor challenge, tumors were 143.3±3.33 mm$^2$ and 151.7±7.27 mm$^2$ for saline-treated Ltα−/− and B6 mice, respectively; treatment with DC-SLC/CCL-21 resulted in reduced tumor growth of 69.67±10.33 mm$^2$ in Ltα−/− and 45.5±3.5 mm$^2$ in B6 animals ($p<0.001$ for DC-SLC/CCL-21 versus saline for both groups of mice). Taken together, the data demonstrate that treatment of s.c. B16 melanoma with DC-SLC/CCL-21 results in the activation and differentiation of T cells into IFN-γ-secreting effectors in the absence of a DLN. Furthermore, inhibition of tumor growth by direct administration of DC-SLC/CCL-21 does not require the presence of peripheral LNs. The data further suggested that the DC-SLC/CCL-21 induce an increase in T cell infiltration to the tumor, in part through an increase in tumor retention of ex vivo-derived DC and not through enhanced migration to the LN.

Figure 9:
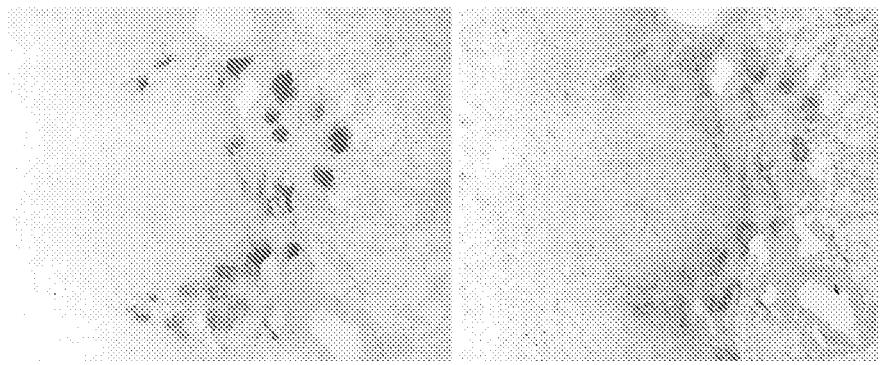
FIGS. 9, 10, and 11 are photographs showing the presence of ectopic lymph node-like structures in some (Case 1, FIG. 9; Case 2, FIG. 10; Case 4, FIG. 11), but not all (Case 3, FIG. 10), human lung, melanoma, and colorectal solid tumors as identified by histologic analysis. Similar examples were observed in human pancreatic cancer as well. Preliminary data have shown that these ectopic lymph node-like structures are likely created by endogenous chemokines secreted by the tumor; their appearance also appears to directly correlate with better prognosis in patients.
Figure 10:
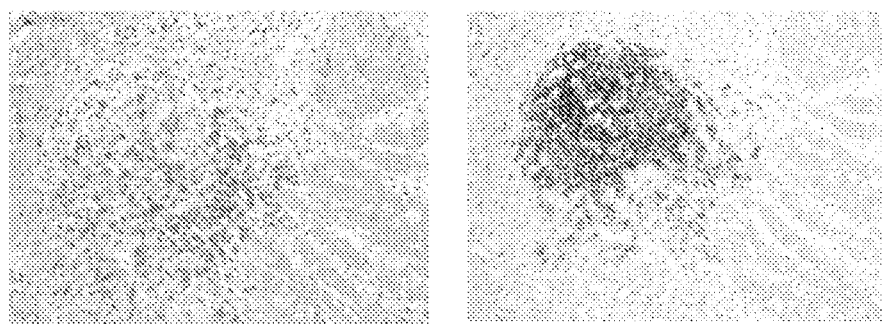
Figure 10:
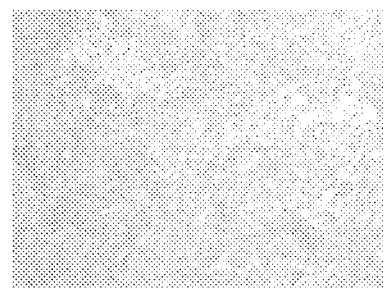
Figure 10:
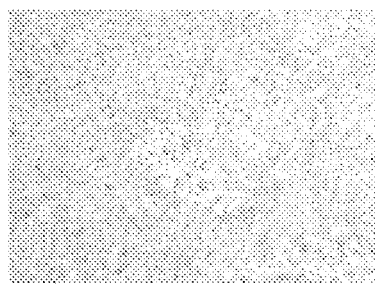
Figure 11:
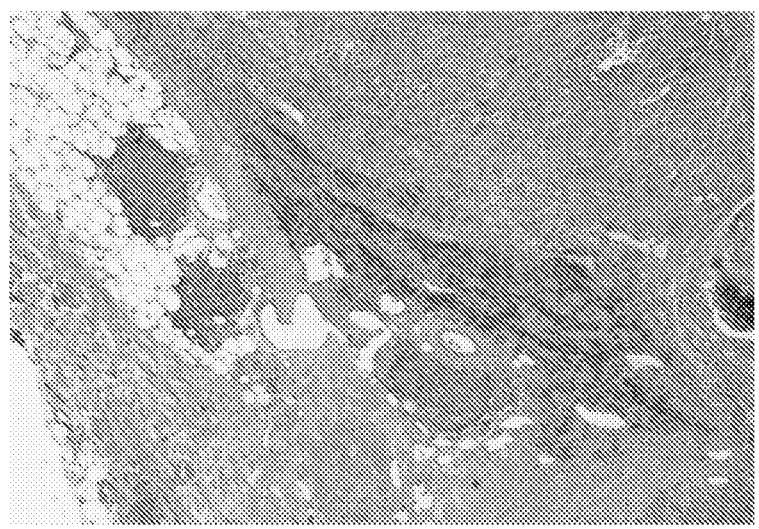

These data demonstrated for the first time that effective T cell priming could occur both extranodally and extrasplenically (in Ltα−/− mice that we had also splenectomized), and result in measurable, enhanced antitumor effects in vivo, through creation of new, functional bioengineered lymph nodes. This latter finding has relevance to the recent, intriguing finding of ectopic lymph nodes present within human solid tumor masses that appear to correlate with better patient prognosis (Coppola and Mulé, J Clin Oncol. 26(27):4369-70, 2008.). In this regard, the presence vs. absence of these ectopic lymph node structures was evaluated in human solid tumors (Coppola et al., Ectopic lymphoid tissue in colonic adenocarcinoma. [abstract]. In: Proceedings of the 100th Annual Meeting of the American Association for Cancer Research; 2009 Apr. 18-22; Denver, Colo. Philadelphia (PA): AACR; 2009. Late Breaking Abstract nr 9047.). FIGS. 9, 10, and 11 show examples in lung, melanoma, and colorectal cancers. Other tumor histologies are currently under investigation. Of interest, the presence of these ectopic lymph nodes appears to correlate with a molecular signature pattern of expressed chemokine genes by tumor microarrays and metagene analysis as well as better prognosis.

Example 7

Human DC-SLC/CCL-21

Figure 12:
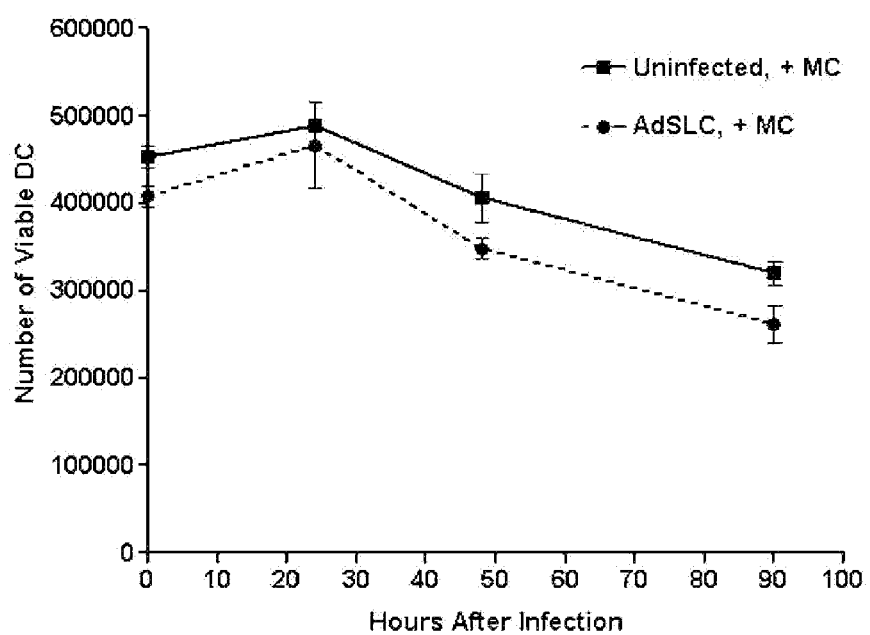
FIG. 12 is a line graph showing the viability of mature, AdSLC/CCL-21-transduced human DC over time. Uninfected or AdSLC/CCL-21-transduced DC were placed in culture and matured by the addition of 1× monocyte conditioned medium. At various time points following infection, numbers of viable DC were quantitated by manual counting using a hemacytometer and trypan blue exclusion. Values represent average counts±the SEM. Graph is representative of three experiments.

Based on the murine work described, human DC were genetically modified to secrete human SLC/CCL-21 (Terando et al., Cancer Gene Ther. 11(3):165-73, 2004.). Human peripheral blood mononuclear cells were placed in culture, depleted of lymphocytes, and cultured in human GM-CSF (100 ng/ml) and IL-4 (50 ng/ml) for 6 days to generate immature DC. DC phenotype was confirmed by FACS analysis that demonstrated low levels of CD14, and high levels of HLA-DR. An adenoviral vector with E1 and E3 deletions that contained the cDNA for human SLC/CCL-21 was used to transduce immature human monocyte-derived DC. Viability of DC-SLC/CCL-21 was determined using trypan blue exclusion. Although adenoviral infection has a cytopathic effect on human DC, which increased with higher multiplicities of infection, DC-SLC/CCL-21 viability was comparable to that of untransduced DC at an MOI of 10,000 particles per cell (FIG. 12).

Figure 13:
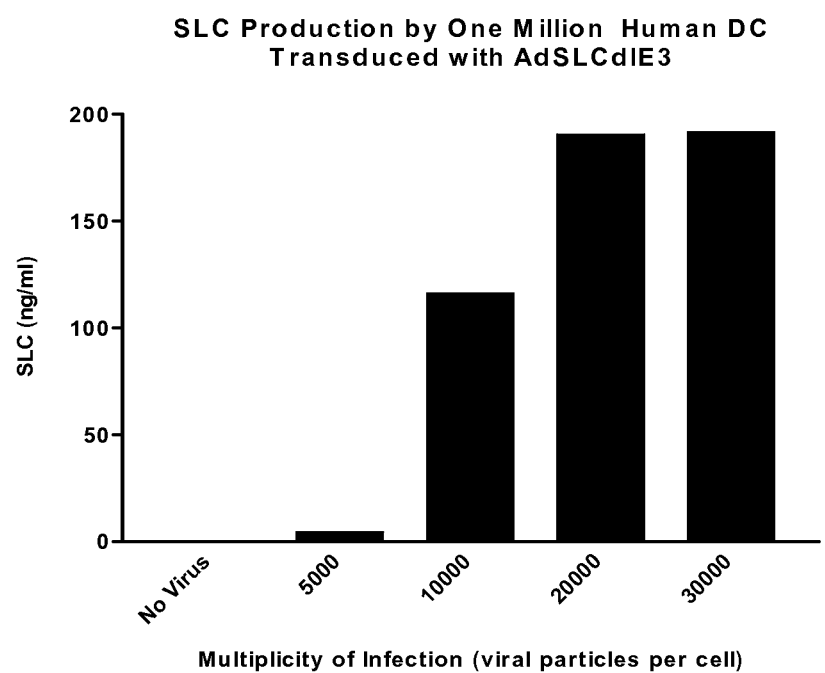
FIG. 13 is a bar graph depicting the amount of SLC/CCL-21 produced by one million human DC transduced with AdSLCdIE3. One million DC-SLC/CCL-21 were found to consistently produce greater than 100 ng/ml of functional SLC/CCL-21 protein following transduction.

In order to quantify the amount of functional SLC/CCL-21 elaborated by AdSLC/CCL-21 infected DC (AdSLC/CCL-21-DC), an in vitro microchemotaxis assay was performed using the supernatant from AdSLC/CCL-21-DC to attract T cells through a 5-micron pore size membrane. SLC/CCL-21 concentrations in unknown samples were extrapolated from a standard curve using nonlinear regression. One million DC-SLC/CCL-21 were found to consistently produce greater than 100 ng/ml of functional SLC/CCL-21 protein at 48 hours following transduction (FIG. 13).

Figure 14:
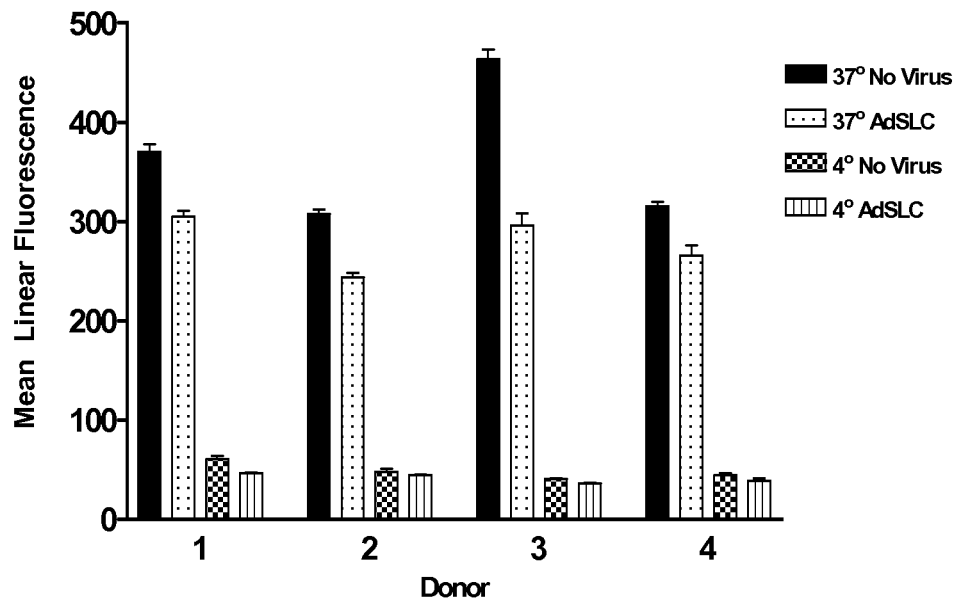
FIG. 14 is a bar graph showing the phagocytic activity of SLC/CCL-21 gene-modified human DC to take up fluorescein-labeled dextran particles was not appreciably different from that of unmodified DC as determined by FACS analysis.

Phenotypic analyses demonstrated that expression of costimulatory and MHC class II molecules by human DC, following adenoviral infection and subsequent maturation, was preserved (Terando et al., Cancer Gene Ther. 11(3):165-73, 2004.). To determine whether the phagocytic capability of transduced DC was also preserved, as the ability of gene-modified DC to take up particulate material is critical for tumor antigen processing and presentation in vivo, fluorescein-labeled dextran particles were exposed to transduced and untransduced DC. Half of the cells were kept at 4° C. as a negative control. Two hours following addition of the labeled dextran particles, FACS analysis was performed to determine the relative amount of material that was taken up by the different samples. Phagocytic activity by gene-modified DC was not appreciably different from that of unmodified DC (FIG. 14).

In summary, through the use of an adenoviral vector containing the gene for human SLC/CCL-21, human DC have been transduced to produce biologically active human SLC/CCL-21 that chemoattracts T cells in vitro. Though a cytopathic effect of adenoviral infection on DC was seen, which was directly related to the amount of adenovirus the DC were exposed to, DC viability was largely preserved at 10,000 particles per cell. Moreover, DC phenotype and phagocytic function were preserved following gene modification. Effects of adenoviral gene transfer on the ability of DC to prime T cells in vitro was not compromised (Terando et al., Cancer Gene Ther. 11(3):165-73, 2004.).

Culture of Human DC

Human DC are cultured by isolating peripheral blood mononuclear cells (PBMC) from healthy or cancer donors by leukapheresis and cryopreserved in liquid nitrogen until use. After thawing, PBMC are resuspended in serum-free X-VIVO 15 and cultured overnight. Nonadherant cells are removed and the remaining adherent monocytes are cultured in X-VIVO 15 medium containing 100 ng/ml GM-CSF and 50 ng/ml IL-4. After 7 days of culture, adherent and nonadherent cells are harvested.

Gene Modification of Human DC

Following harvest, human DC are resuspended at $5\times10^6$ cells/ml in PBS. Various vp/cell of adenovirus expressing recombinant chemokine genes are added to the DC and incubated for 2 hours at 37° C. Transduced DC are resuspended at $1\times10^6$ cells/ml X-VIVO 15 containing GM-CSF and IL-4, and incubated for 24 hours at 37° C. Supernatants are collected and the optimal concentration of each adenovirus are determined by T cell, NK, or B cell migration in a chemotaxis assay as described above. For Ad-SLC/CCL-21, the optimal concentration of virus has been determined to be ~40,000 vp per DC.

Purification of Human Cell Subsets

Magnetic beads for cell separations and separation kits are purchased from Miltenyi Biotec. CD3$^+$ T cells are purified from donor PBL using the Pan T cell Isolation Kit II. CD4$^+$ or CD8$^+$ T cell subsets are purified from PBL using the CD4$^+$ or CD8$^+$ T cell Isolation Kit II, respectively. CD4$^+$CD25$^+$ T cells are purified from PBL using the CD4$^+$CD25$^+$ Regulatory T cell Isolation Kit. For isolation of Tcm and Tem, CD8 purified T cells are stained with anti-CCR7-APC antibodies, followed by staining with anti-APC MACS beads. NK cells are isolated from donor PBL using the NK cell Isolation Kit. B cells are isolated from PBL using the B cell Isolation Kit II. Cell separations are performed on an autoMACS Separator system Immature and mature DC are generated from peripheral blood mononuclear cell leukapheresis collections as previously described. Purification of subsets are verified by flow cytometric analysis.

Example 8

Screening Recombinant Chemokines for Specific, Positive Biologic Activities on Immune Cell Subtypes An initial step of the process is to determine which chemokines cause the migration of which immune cell types. There are many immune cell types, such as CD4$^+$ T cells, CD8$^+$ T cells, NK cells, and B cells. Each cell type migrates in response to different chemokines. Hence, the first step involves an assay for migration (chemotaxis) to screen various immune cell types against the 48 (to date) known chemokines, with the end result that each immune cell type is matched to the chemokine(s) that induces its migration. Furthermore, it is contemplated that, as additional chemokines are identified, these chemokines can be included in the screening.

Recombinant chemokines are screened by in vitro assays and those that offer the most promising biologic activities for inducing or boosting antitumor immunity when combined with TL-DC are selected. Rather than focusing on attempts to deliver greater numbers of ex vivo generated DC to lymph nodes to trigger antitumor immunity, the current strategies are to deliver immune cells to the site(s) of administered DC through the use of chemokines. As mentioned above, to date, there are four classes of chemokines (C, CC, CXC, and CX3C). Of importance, the total number of distinct molecules comprising these four classes is 48 (Table 2).

TABLE 2

Chemokines and Their Receptors

| Name | Gene | Other name(s) | Receptor | Uniprot |
|---|---|---|---|---|
| CC chemokines | | | | |
| CCL1 | Scya1 | I-309, TCA-3 | CCR8 | |
| CCL2 | Scya2 | MCP-1 | CCR2, CCR2 | P13500 |
| CCL3 | Scya3 | MIP-1a | CCR1 | P10147 |
| CCL4 | Scya4 | MIP-1β | CCR1, CCR5 | P13236 |
| CCL5 | Scya5 | RANTES | CCR5 | P13501 |
| CCL6 | Scya6 | C10, MRP-2 | CCR1 | P27784 |
| CCL7 | Scya7 | MARC, MCP-3 | CCR2 | P80098 |
| CCL8 | Scya8 | MCP-2 | CCR1, CCR2B, CCR5 | P80075 |
| CCL9/CCL10 | Scya9 | MRP-2, CCF18, MIP-1 | CCR1 | P51670 |
| CCL11 | Scya11 | Eotaxin | CCR2, CCR3, CCR5 | P51671 |
| CCL12 | Scya12 | MCP-5 | | Q62401 |
| CCL13 | Scya13 | MCP-4, NCC-1, Ckβ10 | CCR2, CCR3, CCR5 | Q99616 |
| CCL14 | Scya14 | HCC-1, MCIF, Ckβ1, NCC-2, CCL | CCR1 | Q16627 |
| CCL15 | Scya15 | Leukotactin-1, MIP-5, HCC-2, NCC-3 | CCR1, CCR3 | Q16663 |
| CCL16 | Scya16 | LEC, NCC-4, LMC, Ckβ12 | CCR1, CCR2, CCR5, CCR8 | O15467 |
| CCL17 | Scya17 | TARC, dendrokine, ABCD-2 | CCR4 | Q92583 |
| CCL18 | Scya18 | PARC, DC-CK1, AMAC-1, Ckβ7, MIP-4 | | P55774 |
| CCL19 | Scya19 | ELC, Exodus-3, Ckβ11 | CCR7 | Q99731 |
| CCL20 | Scya20 | LARC, Exodus-1, Ckβ4 | CCR6 | P78556 |
| CCL21 | Scya21 | SLC, 6Ckine, Exodus-2, Ckβ9, TCA-4 | CCR7 | O00585 |
| CCL22 | Scya22 | MDC, DC/β-CK | CCR4 | O00626 |
| CCL23 | Scya23 | MPIF-1, Ckβ8, MIP-3, MPIF-1 | CCR1 | P55773 |
| CCL24 | Scya24 | Eotaxin-2, MPIF-2, Ckβ6 | CCR3 | O00175 |
| CCL25 | Scya25 | TECK, Ckβ15 | CCR9 | O15444 |
| CCL26 | Scya26 | Eotaxin-3, MIP-4a, IMAC, TSC-1 | CCR3 | Q9Y258 |
| CCL27 | Scya27 | CTACK, ILC, Eskine, PESKY, skinkine | CCR10 | Q9Y4X3 |
| CCL28 | Scya28 | MEC | CCR3, CCR10 | Q9NRJ3 |
| CXC chemokines | | | | |
| CXCL1 | Scyb1 | Gro-a, GRO1, NAP-3, KC | CXCR2 | P09341 |
| CXCL2 | Scyb2 | Gro-β, GRO2, MIP-2a | CXCR2 | P19875 |
| CXCL3 | Scyb3 | Gro-?, GRO3, MIP-2β | CXCR2 | P19876 |
| CXCL4 | Scyb4 | PF-4 | CXCR3B | P02776 |
| CXCL5 | Scyb5 | ENA-78 | CXCR2 | P42830 |
| CXCL6 | Scyb6 | GCP-2 | CXCR1, CXCR2 | P80162 |
| CXCL7 | Scyb7 | NAP-2, CTAPIII, β-Ta, PEP | | P02775 |
| CXCL8 | Scyb8 | IL-8, NAP-1, MDNCF, GCP-1 | CXCR1, CXCR2 | P10145 |
| CXCL9 | Scyb9 | MIG, CRG-10 | CXCR3 | Q07325 |
| CXCL10 | Scyb10 | IP-10, CRG-2 | CXCR3 | P02778 |
| CXCL11 | Scyb11 | I-TAC, β-R1, IP-9 | CXCR3 | O14625 |
| CXCL12 | Scyb12 | SDF-1, PBSF | CXCR4 | P48061 |
| CXCL13 | Scyb13 | BCA-1, BLC | CXCR5 | O43927 |
| CXCL14 | Scyb14 | BRAK, bolekine | | O95715 |
| CXCL15 | Scyb15 | Lungkine, WECHE | | Q9WVL7 |
| CXCL16 | Scyb16 | SRPSOX | | Q9H2A7 |
| CXCL17 | VCC-1 | DMC, VCC-1 | | Q6UXB2 |

TABLE 2-continued

Chemokines and Their Receptors

| Name | Gene | Other name(s) | Receptor | Uniprot |
|---|---|---|---|---|
| C chemokines | | | | |
| XCL1 | Scyc1 | Lymphotactin a, SCM-1a, ATAC | XCR1 | P47992 |
| XCL2 | Scyc2 | Lymphotactin β, SCM-1β | XCR1 | Q9UBD3 |
| CX3C chemokines | | | | |
| CX3CL1 | Scyd1 | Fractalkine, Neurotactin, ABCD-3 | CX3CR1 | P78423 |

Aliquots of many of recombinant chemokine proteins and the expression plasmids for the chemokines are obtained, e.g., through commercial vendors (e.g., PeproTech, Rocky Hill, N.J. or R & D Systems, Minneapolis, Minn.). Using sensitive in vitro assays for cell migration and for immune cell activation as those used with SLC/CCL-21, each of the 48 distinct chemokines are screened for activity in eliciting migration and/or enhancing tumor antigen(s) activation of highly-enriched populations of naïve T cells (both CD4$^+$ and CD8$^+$), T central memory cells (Tcm), T effector memory cells (Tem), T regulatory cells, natural killer (NK) cells, immature and mature DC, as well as B cells, e.g., from tumor-bearing mice or humans. The cells are loaded with tumor antigen(s), e.g., in the form of known whole proteins, known peptides, cDNAs or mRNAs, or whole live or killed (necrotic or apoptotic) autologous or allogeneic tumor cells. Both mouse and human immune cell subsets are examined. Based on the outcome of these assays, single and multiple chemokines are then selected for further screening in vivo for creation of functioning bioengineered lymph node structures.

The screening includes T regulatory cells to eliminate chemokines that selectively or predominantly cause the attraction and/or activation of these unwanted suppressive cells in the in vivo design of any ectopic bioengineered lymph node structure (e.g., CCL-20; 8).

Figure 15:
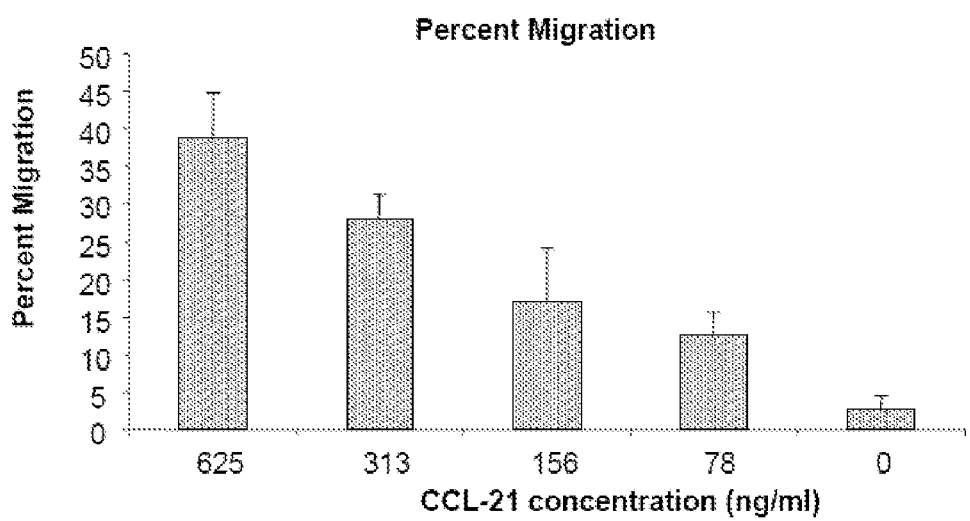
FIG. 15 is a bar graph depicting the results of a representative 96-well format microchemotaxis assay using SLC/CCL-21 and $CD3^+$ T cells enriched from the spleens of B6 mice.
Figure 16:
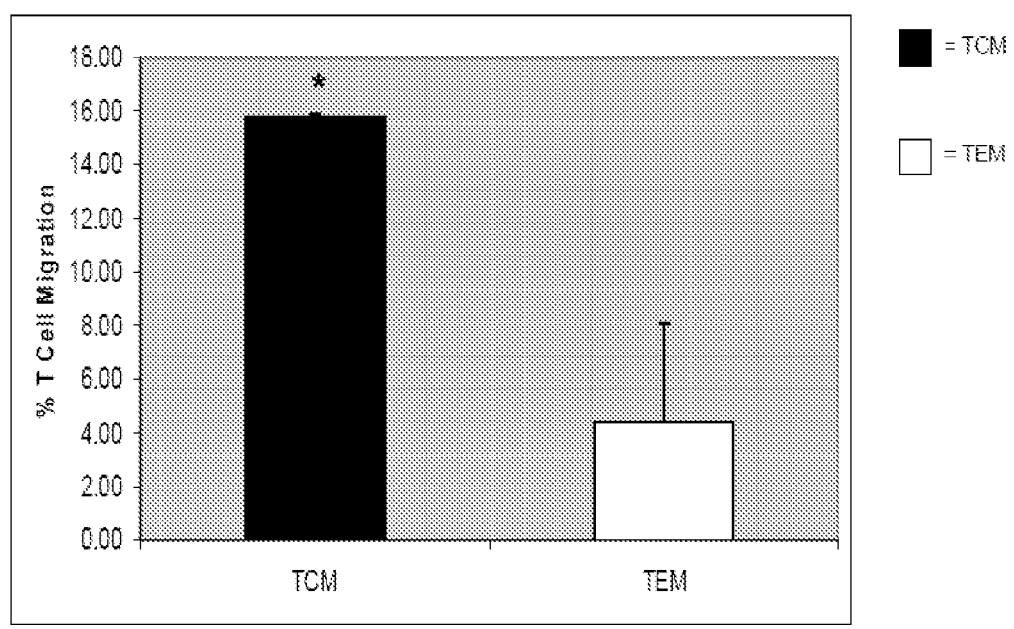
FIG. 16 is a bar graph showing chemoattraction of mouse T central memory cells (Tcm) and T effector memory cells (Tem) by SLC/CCL-21 using an improved microchemotaxis assay. *, $p<0.05$.
Figure 17:
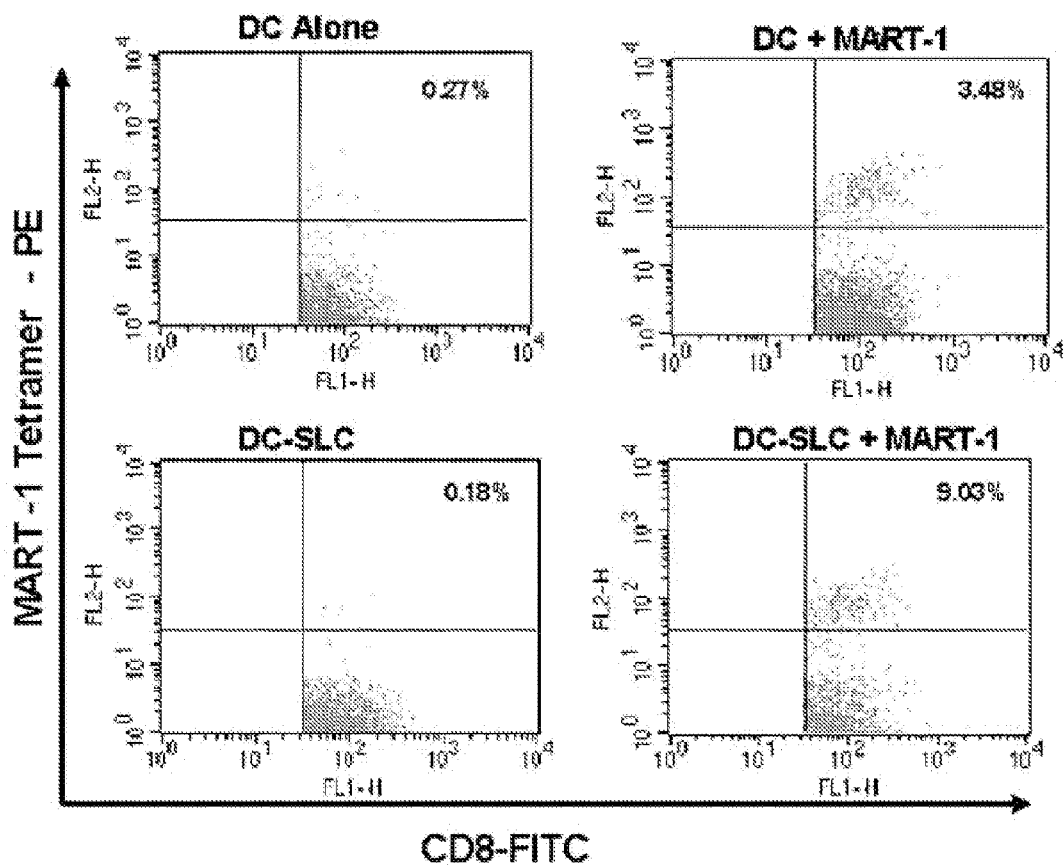
FIG. 17 is a series of scatter plots showing that AdSLC/CCL-21-transduced human DC successfully enhance priming of naïve T lymphocytes in vitro. Uninfected and AdSLC/CCL-21-transduced, HLA-A201-positive DC were pulsed with MART-1 peptide, and used to stimulate nylon-wool-purified, autologous T cells. Following two stimulations, MART-1 tetramer staining was performed. Results are representative of three experiments.
Figure 18:
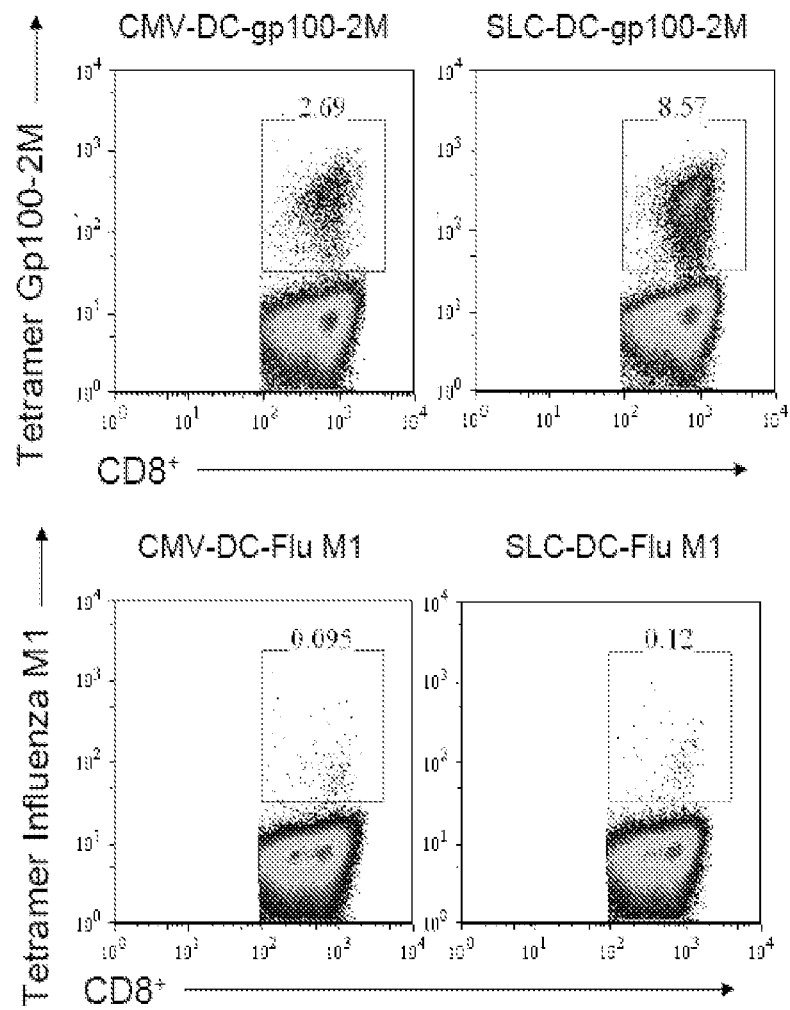
FIG. 18 is a series of scatter plots showing human SLC/CCL-21-producing DC can enhance T cell priming to the gp100-2M melanoma peptide in vitro. Data show melanoma patient T cells after two CMV/SLC/CCL-21 DC in vitro re-stimulations.
Figure 19:
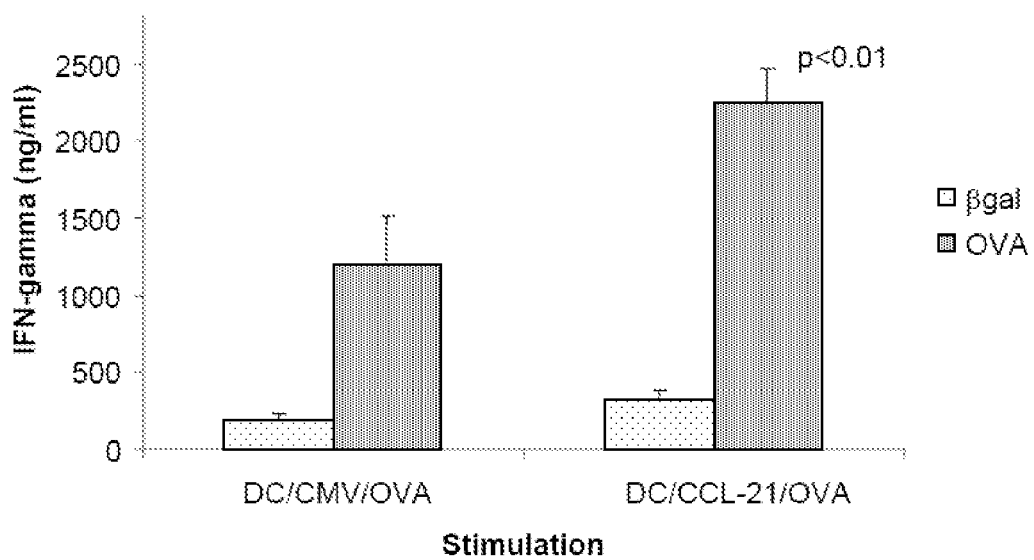
FIG. 19 is a bar graph showing mouse DC-SLC/CCL-21 can enhance antigen-specific T cell function. T cells from DC-OVA$_{siinfeckl}$ vaccinated mice were co-cultured for 7 days with DC-AdCMV+OVA$_{siinfeckl}$ or DC-AdSLC/CCL-21+OVA$_{siinfeckl}$. T cells were restimulated for 48 hours with β-gal or OVA peptide. IFN-gamma ELISA was performed.

A microchemotaxis assay adapted to a 96-well format is used for higher throughput testing of all known chemokines to be studied. This format allows for very small numbers of immune cells to be used. Whole, single cell suspensions of freshly prepared spleens and lymph nodes of mice bearing 10-day B16 melanoma in the skin or in the lungs (as a result of 1×10$^5$ viable tumor cells injected s.c. or intravenously (i.v.), respectively) are used. T cell subset, NK cell, or B cell migration from the loaded, whole (unfractionated) cell population plated in quadruplicate (or more to obtain adequate cell numbers for analysis), induced by various chemokines, are measured in a 96-well 5 μm pore ChemoTx system (Neuro Probe, Gaithersburg, Md.). Complete medium (CM, 300 μl) containing 0-625 ng/ml recombinant murine chemokine is plated in triplicate. The 5 μm pore chemotaxis membrane is added to the plate. The fresh, whole (unfractionated) cell population (1×10$^5$ cells in 50 μl of CM) is placed on the membrane surface above each well containing the chemokine. The plate is incubated for 90 minutes at 37° C. At the end of the incubation, the membrane is removed and the cells in the lower wells are harvested (triplicate wells are pooled), counted, and stained by the appropriate relevant mAbs, and analyzed by FACS for the presence of CD4$^+$ T cells, CD8$^+$ T cells, Treg, NK, and/or B cells. If necessary to increase resolution/sensitivity, or to further confirm the results, highly-enriched cell populations can be used. In this case, the purified immune cell subsets are loaded at 1×10$^4$ cells and the assay is run as described for the whole, unfractionated single cell suspensions. After removal of the membrane at 90 minutes, however, 10 μl of 11X Cyquant NF (Invitrogen) is added to each well. The plate is incubated for 15 minutes at 37° C. The fluorescence intensity of each well is measured on a fluorescent plate reader (Victor 2, Perkin Elmer). The number of migrated cells in each sample is determined by inserting the fluorescence intensity into the standard curve. FIG. 15 shows the results of a representative 96-well format microchemotaxis assay using SLC/CCL-21 and CD3$^+$ T cells enriched from the spleens of B6 mice. T central memory cells (Tcm) and T effector memory cells (Tem) were generated using standard, published procedures and have been examined for their respective chemoattraction by SLC/CCL-21 using the microchemotaxis assay (FIG. 16). Using the melanoma-associated peptide MART-1, SLC/CCL-21 was previously shown to boost the priming of naïve T cells in vitro (Terando et al., Cancer Gene Ther. 11(3):165-73, 2004.) (FIG. 17). The percentage of CD8$^+$/MART-1 tetramer$^+$ T cells that were generated by DC-SLC/CCL-21 was shown to be significantly greater than those produced by control DC. This novel finding has been reproduced in a series of separate studies employing a second human melanoma peptide, namely gp100-2M (FIG. 18), as well as in the mouse, employing a model OVA peptide (FIG. 19). These results using AdvSLC/CCL-21 infected DC can be replicated by the addition of recombinant SLC/CCL-21 (100-200 ng/ml) to peptide-loaded DC, allowing for higher/faster throughput screening of the other chemokines to be done in the absence of Adv vector-mediated gene transduction.

In Vitro Murine Immune Cell Stimulations and Analysis

Direct activation of immune subsets (freshly harvested CD4$^+$, or CD8$^+$ T cells, NK cells, and B cells from B16 melanoma bearing mice) is performed in 96-well plates adding 1×10$^4$ cells with increasing amounts of chemokine (ranging from 0-500 ng/ml) only. Ample precedent exists for chemokines directly activating immune cell subsets (38, 39). After various time points (0-5 days), the immune cell subsets are harvested, stained by the appropriate relevant mAbs, and examined by FACS for the presence of known, cell surface-expressed activation markers (Lai et al., J. Immunol. 160(8): 3861-8, 1998.). For tumor-specific T cell stimulations, TL-DC are added to the assay, with or without the chemokine of interest. The freshly prepared T cell subsets are added at a 1:10 or 1:20 ratio in CM. For the second stimulation, 10 IU/ml IL-2 or IL-7 (Chiron Corporation, Emeryville, Calif.) are added to the medium, if needed (Jicha et al., J Exp Med. 174(6):1511-5, 1991.).

ELISA Assay

To determine IFN-γ expression by T cells and NK cells after stimulation with and without TL-DC and with and without chemokine, supernatants are collected and cytokine measured by commercially available ELISA kits (e.g., the BD OptEIA Mouse ELISA Set (BD Biosciences).

In Vitro Human T Cell Stimulations

Following gene modification with chemokine-expressing adenovirus, HLA-02 positive DC are cultured in X-VIVO media supplemented with GM-CSF, IL-4, and a maturation cocktail containing 100 U/ml IL-6, 10 ng/ml IL1, 1 µg/ml PGE2, and 10 ng/ml TNF-α. Melanoma associated peptides gp100-2M (IMDQVPFSV), gp100$_{209-217}$ (ITDQVPFSV), or control peptide influenza M1 (GILGFVFTL) at a concentration of 10 µg/ml are also added to the DC. After 24 hours, the DC are counted and combined with MACS-purified (Miltenyi Biotec) CD8$^+$ T cells at a 1:10 ratio in serum free X-VIVO 15 medium. After 7 days, T cells are harvested and restimulated as above. For the second stimulation, 10 IU/ml IL-2 is added to the medium (Chiron Corporation, Emeryville, Calif.).

Tetramer Staining of Human T Cells

Following two stimulations by peptide-pulsed DC, T cells are harvested, counted, and stained using anti-human CD8 antibody, 7-AAD (Pharmingen, San Diego, Calif.), and the iTAG MHC tetramer: HLA-A02 melanoma gp100-2M-PE, HLA-A02 gp100-PE, or HLA-A02 flu M1-PE (Becton-Coulter Inc., San Diego, Calif.). FACS analysis is performed.

Example 9

Tcm and Tem Cell Subsets

Two additional immune cell subsets uniquely responding to certain chemokines identified in the screening process, namely T central memory cells (Tcm) and T effector memory cells (Tem), are studied to address the therapeutic potential of different tumor-reactive CD8$^+$ T cell memory subsets. Tcm and Tem are segregated on the basis of phenotypic markers, functional attributes, and migratory properties. Tcm have been shown to be superior to Tem in conferring protective immunity against viral or bacterial challenge as well as in conferring superior antitumor immunity. Tcm and Tem are found in both human and mice. For this purpose, T cells derived from a p-mel mouse and DC pulsed with the relevant melanoma peptide are employed. Several studies have demonstrated the technique of culturing CD8$^+$ T cells derived from transgenic p-mel mice, which recognize MHC I restricted human gp100$_{25-33}$ (hgp100) peptide via its Vβ13 TcR (42-44). Human gp100$_{25-33}$ (hgp100), the altered peptide ligand for mouse gp100$_{25-33}$, permitted CD8$^+$ T cells isolated from p-mel mice to lyse B16 melanoma (Overwijk et al., J Exp Med. 188(2):277-86, 1998.). Whole splenocytes derived from p-mel mice are cultured for 7 days in complete medium (CM) containing either 10 ng/ml rhIL-2+10 µg/ml hgp100 to generate Tem or 10 ng/ml rmIL-15+10 µg/ml hgp100 to generate Tcm. For highest purity, cultures of Tcm and Tem are stained with anti-CCR7-APC antibodies, followed by incubation with anti-APC MACS beads for positive/negative selections. Purification of subsets is verified by flow cytometric analysis (see also FIG. 16). Additional studies are conducted using B16 tumor infiltrating lymphocytes (TIL). Studies are performed in vivo once sets of chemokines highly selective for recruitment and activation of TIL, Tem, and Tcm are identified.

Example 10

Evaluate the Capacity of Chemokine(s) Gene-Modified TL-DC to Mediate an Enhanced Therapeutic Antitumor Response in Mice TL-DC are gene-modified using adenovirus vector constructs to produce the selected chemokines and evaluated in animal tumor models. Candidates from the panel of 48 chemokines are selected to design a fully functioning, optimized bioengineered lymph node structure with the chemokine(s) gene-modified TL-DC serving as the critical APC within the structure, namely those for CD4$^+$ T cells, CD8$^+$ T cells, NK cells, and B cells, to achieve both a cellular and humoral immune response. With respect to the latter, it has been shown that administration of anti-B16 melanoma antibody can cause a substantial and consistent reduction in established metastases (Eisenthal et al., Cancer Res. 47(11): 2771-6, 1987.), thus justifying the inclusion of B cells in the strategy. NK cells are also included given that known functional links exist between innate lymphocytes and DC, demonstrating that reciprocal activations follow on from NK/DC interactions (Reschner et al., Clin Exp Immunol. 152(2):219-26, 2008.; Zitvogel et al., Curr Top Microbiol Immunol. 298: 157-74, 2006.; Fernandez et al., Nat. Med. 5(4):405-11, 1999.). The cross-talk between NK cells and DC can lead to innate lymphocyte activation and DC maturation, and the final outcome of these cellular interactions can have a dramatic impact on the quality and strength of the downstream immune response.

A separate adenovirus vector is constructed for each candidate chemokine (similar to what was done for SLC/CCL-21) and used separately to infect TL-DC. The separately transduced TL-DC are first tested to establish the level of chemokine production by either ELISA or microchemotaxis assay. A dose titration of each chemokine(s) producing TL-DC injected s.c. is separately performed in B16 melanoma bearing mice (e.g., 1×10$^4$, 1×10$^5$, 1×10$^6$) to ascertain the optimal cell number needed for recruiting and activating the respective host immune cell subset to the injection site. Analysis of the level of recruitment and activation is performed as described with SLC/CCL-21 (Kirk et al., Cancer Res. 61(5):2062-70, 2001.; Kirk et al., Cancer Res. 61(24): 8794-802, 2001.). The injected dose is anticipated to fall within the range of 1×10$^6$ TL-DC based on that with TL-DC-SLC/CCL-21. Once the individual doses are optimally established, the chemokine(s)-producing TL-DC are pooled at those doses to determine whether a fully functioning, bioengineered lymph node structure is formed. The latter is evaluated by both histology (immunohistochemistry) and FACS analysis of the harvested, disaggregated biopsy site.

For treatment experiments, 1×10$^5$ melanoma cells are injected s.c. in the left flank of B6 mice. Ten days after tumor challenge, mice receive a pooled chemokine(s)-producing TL-DC vs. Adv-GFP control TL-DC either in the contralateral flank or intratumorally and are monitored for tumor progression/regression. Tumors are monitored every 2-3 days with Vernier calipers and the largest perpendicular measurements of tumor area (in mm$^2$) recorded. Data are reported as the average tumor area±SE, with five or more mice/group. The impact on experimentally-induced, macro visceral metastases are also evaluated. In this case, mice receive the B16 melanoma cells i.v. to establish pulmonary nodules and receive the pooled chemokine(s)-producing TL-DC vs. Adv-GFP control TL-DC on day 10. Mice are euthanized at day 21 and the lung nodules enumerated, as described previously (Gorbachev et al., J. Immunol. 178(4):2278-86, 2007.; Shurin et al., J. Immunol. 174(9):5490-8, 2005.; Zhang et al., J. Immunol. 174(9):5856-63, 2005.). Standard survival experiments are also incorporated whereby in additional experiments, the percentage of surviving animals is recorded over time. Additional experiments employ mice harboring both 10-day s.c. tumor and pulmonary nodules. All comparisons of tumor size and survival are made between groups receiving chemokine(s)-producing TL-DC and Adv-GFP control TL-DC.

Example 11

Multiple, Independent Bioengineered Lymph Node Structures

Pooled chemokine(s)-producing TL-DC are injected at multiple, independent sites to create multiple, independent functioning bioengineered lymph node structures concurrently. The injections can also be staggered to create additional new structures over time. These structures may prove to act independently of each other, raising the intriguing possibility of creating completely different functioning bioengineered lymph node structures in the same animal or human by injecting pools of different chemokine(s)-producing TL-DC. Moreover, adoptive transfers of additional, freshly prepared immune cell subsets given i.v. to augment the creation/size/function of bioengineered lymph node structures and/or anti-tumor immunity is conceivable.

Example 12

Harvest of Tumor and Bioengineered Lymph Node Structures for Immunohistochemistry and FACS Analysis For immunohistochemical analysis of location of immune cell subsets, s.c. tumors, lungs containing pulmonary nodules (for the mouse only), and skin containing the area of the bioengineered lymph node structure are harvested at various empiric time points and snap frozen in liquid $N_2$, and sections are analyzed for the presence of $CD4^+$ T cells, $CD8^+$ T cells, NK cells or B cells with specific antibodies (e.g., from Serotec, Raleigh, N.C.). Cells are counted in 10 high powered fields (×40) per section (two sections/sample) in a blinded fashion.

To quantify immune cell subset infiltration, s.c. tumors, lungs containing pulmonary nodules (for the mouse only), and skin containing the area of the bioengineered lymph node structure are harvested (at various empiric time points) and digested for 2 hours at room temperature in 1 mg/ml collagenase (type IV), 1500 units/ml DNase I (type IV), and 1 mg/ml hyaluronidase (type V; all from Sigma) with constant stirring. Digested tumors are passed over a 70 μm nylon mesh, washed once with PBS, and resuspended in PBS+3% BSA to approximately $1\times10^6$ cells/ml. Polystyrene beads (15 μm diameter) are added to the samples to achieve a concentration of $5\times10^5$ beads/ml. Samples are stained for the presence of $CD4^+$ T cells, $CD8^+$ T cells, NK cells or B cells with PE-conjugated antibodies (PharMingen).

To determine the level of activation in T cells accumulating in the bioengineered lymph node structure or tumor, single cell suspensions (prepared as described above) are stained with fluorescein (FITC)-conjugated antibodies to CD11b and B220, PE-conjugated antibodies to CD25 or CD62L, and Cy-Chrome-conjugated antibodies to CD4 or CD8. Samples are analyzed by FACS with counting of 50,000 lymphocyte-sized events (based on splenocyte controls). The number of infiltrating $CD4^+$ or $CD8^+$ T cells/tumor are determined by the following equation: (number of PE events/number of bead events)$\times 5\times 10^5\times$ cell sample volume. Because the tumors are of different sizes, the data are normalized to the tumor volume by dividing the total number of infiltrating $CD4^+$ (or $CD8^+$) T cells by the tumor volume using the volume equation V (in $mm^3$)=$0.4(ab^2)$, where a is the long diameter and b is the short diameter. For analysis of T cell subsets and activation in tumors and in the bioengineered lymph node structure(s), $CD62L^+$ or $CD25^+$ events that are also positive for CD4 or CD8 are counted in the $CD11b^-/B220^-$ fraction of cells gated for lymphocyte size by forward and side scatter plot. CD11b is expressed by most of the tumor cells. The expression of either CD11b or B220 on T cells isolated from tumor or LN samples has not been detected.

Detection of Antibody Production

To detect bulk anti-B16 antibodies in the serum, mice are humanely euthanized at varying time points. Serum is collected by cardiac puncture. Alternatively, serum is collected from live mice by bleeding from the retroorbital venus plexus. Serial dilutions of serum are used to stain B16 melanoma cells. Goat-anti-mouse IgG+IgM-PE is used as a secondary stain. Detection of fluorescence is measured by flow cytometry to determine the titer of anti-B16 antibodies, as described previously (Sfondrini et al., Int J. Cancer. 83(1):107-12, 1999.; Nakahara et al., Cancer Res. 66(3):1434-45, 2006.; Fedorovskaia et al., Biull Eksp Biol Med. 76(7):78-80, 1973.). For detection of antibodies at the tumor site, B16 tumors are removed and fixed in 1% paraformaldehyde for 1 hour at 4° C. After rinsing in PBS, tumors are embedded in O.C.T. compound and stored at –80° C. Anti-B16 antibodies bound to tumor cells are detected on cryostat sections by staining with Texas Red-conjugated goat-anti-mouse IgG+IgM secondary antibody. Slides are analyzed by fluorescence microscopy.

Detection of Activated NK Cells

It has been shown that DC-NK cell cross-talk can lead to potent NK cell priming/activation as measured by IFN-γ production (Reschner et al., Clin Exp Immunol. 152(2):219-26, 2008.; Zitvogel et al., Curr Top Microbiol Immunol. 298:157-74, 2006.; Fernandez et al., Nat. Med. 5(4):405-11, 1999.). NK cells ($NK-1.1^+$ by PK136 mAb) are examined in the spleen, tumor and the bioengineered lymph node structure at various time points for the presence of this cytokine (by intracellular staining), as described above.

Example 13

Dose Ranging Trial of Adenovirus CCL-21 Transduced MART-1/gp100/Tyrosinase/NY-ESO-1 Peptide- and KLH-Pulsed Dendritic Cells Matured Using Cytokines in Human Patients with Chemotherapy-Resistant Metastatic Melanoma An SLC/CCL-21 adenovirus vector was constructed as described above and used to infect human DC. The DC were pulsed with MART-1/gp100/Tyrosinase/NY-ESO-1 Peptide- and KLH, and a dose ranging trial was conducted with three treatment cohorts of six patients each, with each patient within a cohort given increasing doses ($10^6$, $10^7$, $2\times10^7$) of the cells, administered i.d. This DC vaccine was injected weekly for two doses, then every two weeks for two doses in each course of therapy, which lasted eight weeks.

The secreted dose of CCL2 was assayed to fall within the range of 41 to 47 ng/mL per $1\times10^6$ TL-DC, as shown in Table 3.

TABLE 3

| COHORT # | COLLECTED APHERESIS PRODUCTS | VACCINES MADE | MEAN VIABLE DC | COHORT TARGET DC/injection | SLC SECRETED (Mean ng/ml per $10^6$ cells per 24 hr) |
|---|---|---|---|---|---|
| 1 | 8 | 29 | 12 million | 1 million | 41 |
| 2 | 6 | 21 | 28 million | 10 million | 47 |

Figure 20:
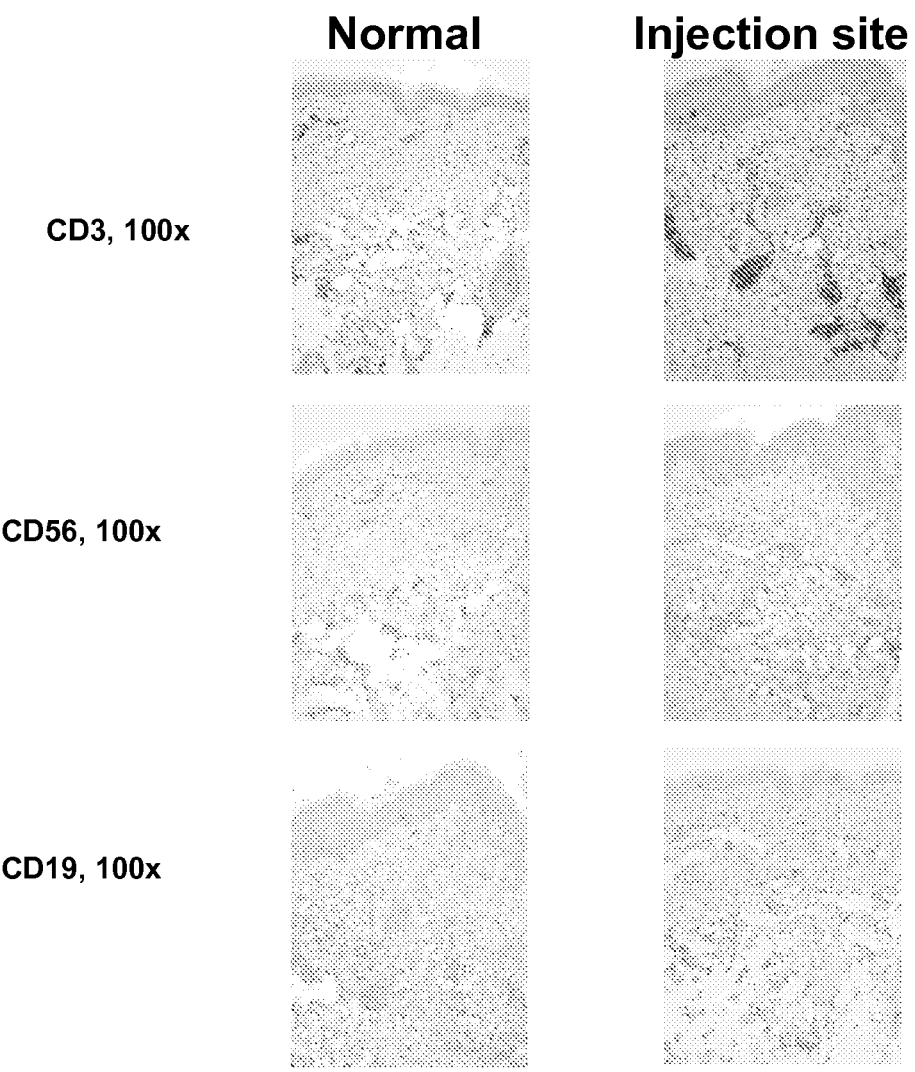
FIG. 20 is a set of six images showing the results of histology staining of a patient that is representative of both Normal tissue (left column) and an Injection Site (right column) Staining for CD3, a T-cell marker (top row) indicates that T-cells have been recruited to the follicle-like structures within an Injection Site. Staining for CD56 (an NK cell marker, middle row) and CD19 (a B cell marker, bottom row) indicated the absence of NK cells or B-cells, respectively, either in the Normal tissue or within the follicle-like structures around the Injection Site.

Analysis of the level of recruitment and activation was performed as described above; the results are shown in FIG. 20. Staining for CD56 (an NK cell marker) and CD19 (a B cell marker) indicated the absence of NK cells or B-cells, respectively, either in the normal tissue or within the follicle-like structures around the injection site.

Staining for CD3, a T-cell marker, indicated that T-cells were recruited to follicle-like structures near the injection site; this indicates that the amount of CCL21 secreted by the cells was enough to selectively attract T cells to the site, as desired.

REFERENCES

1. Yang et al., Cancer Res. 66(6):3205-13, 2006.
2. Ashour et al., Cancer Biol Ther. 6(8):1206-10, 2007.
3. Yousefieh et al., FASEB Journal. 22:1076.15, 2008.
4. Novak et al., Mol Cancer Ther. 6(6):1755-64, 2007.
5. Wu et al., Immunobiology. 213(5):417-26, 2008.
6. Thanarajasingam et al., Cancer Res. 67(1):300-8, 2007.
7. Selvakumaran et al., Proc Amer Assoc Cancer Res, Volume 45, 2004, Abstract nr 1472.
8. Bacon et al., Science. 269(5231):1727-30, 1995.
9. Maghazachi and Al-Aoukaty, FASEB J. 12(11):913-24, 1998.
10. Klebanoff et al., Proc Natl Acad Sci USA. 101(7):1969-74, 2004.
11. Klebanoff et al., Proc Natl Acad Sci USA. 102(27):9571-6, 2005.
12. Overwijk et al., J Exp Med. 198(4):569-80, 2003.
13. Harrison J K, Lukacs N W (eds). *The Chemokine Receptors*. New Jersey: Humana Press, 2007.
14. Legler et al., J Exp Med. 187(4):655-60, 1998.
15. Huang et al., FASEB J. 20(7):896-905, 2006.
16. Barth et al., J. Immunol. 144(4):1531-7, 1990.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising an isolated, engineered dendritic cell comprising exogenous cDNAs encoding exogenous Chemokine (C—C Motif) Ligand (CCL) 8 (CCL-8), CCL-18, and C—X—C Motif Chemokine 13 (CXCL-13).

2. The composition of claim 1, wherein the engineered dendritic cell is selected from the group consisting of a CD14+ blood monocyte-derived dendritic cell, a dermal or interstitial dendritic cell, a Langerhans cell, and a plasmacytoid dendritic cell.

3. The composition of claim 1, wherein the engineered dendritic cell further comprises exogenous cDNA encoding at least one exogenous chemokine selected from the group consisting of CCL-1, CCL-2, CCL-3, CCL-4, CCL-5, CCL-13, CCL-17, CCL-20, CCL-21, CXCL-9, CXCL-10, CXCL-11, CXCL-14, CXCL-16, and Chemokine (C motif) ligand (XCL1).

4. The composition of claim 1, wherein the dendritic cell is antigen-loaded.

5. The composition of claim 4, wherein the antigen is selected from the group consisting of tumor, viral, bacterial, and fungal antigens.

6. The composition of claim 1, wherein the dendritic cell expresses the exogenous CCL-8, CCL-18, and CXCL-13.

7. An isolated, engineered dendritic cell comprising exogenous cDNAs encoding exogenous CCL-8, CCL-18, and CXCL-13.

8. The engineered dendritic cell of claim 7, wherein the dendritic cell further comprises exogenous cDNA encoding at least one exogenous chemokine selected from the group consisting of CCL-1, CCL-2, CCL-3, CCL-4, CCL-5, CCL-13, CCL-17, CCL-20, CCL-21, CXCL-9, CXCL-10, CXCL-11, CXCL-14, CXCL-16, and XCL1.

9. The engineered dendritic cell of claim 7, wherein the dendritic cell is selected from the group consisting of a CD14+ blood monocyte-derived dendritic cell, a dermal or interstitial dendritic cell, a Langerhans cell, and a plasmacytoid dendritic cell.

10. The engineered dendritic cell of claim 7, wherein the dendritic cell is antigen-loaded.

11. The engineered dendritic cell of claim 10, wherein the antigen is selected from the group consisting of tumor, viral, bacterial, and fungal antigens.

12. The engineered dendritic cell of claim 7, wherein the dendritic cell expresses the exogenous CCL-8, CCL-18, and CXCL-13.

13. A composition comprising an isolated, engineered dendritic cell transduced with plasmids, cosmids, or viral vectors encoding exogenous CCL-8, CCL-18, and CXCL-13.

14. The composition of claim 13, wherein the engineered dendritic cell is selected from the group consisting of a CD14+ blood monocyte-derived dendritic cell, a dermal or interstitial dendritic cell, a Langerhans cell, and a plasmacytoid dendritic cell.

15. The composition of claim 13, wherein the engineered dendritic cell is further transduced with vectors encoding at least one exogenous chemokine selected from the group consisting of CCL-1, CCL-2, CCL-3, CCL-4, CCL-5, CCL-13, CCL-17, CCL-20, CCL-21, CXCL-9, CXCL-10, CXCL-11, CXCL-14, CXCL-16, and Chemokine (C motif) ligand (XCL1).

16. The composition of claim 13, wherein the engineered dendritic cell is antigen-loaded.

17. The composition of claim 16, wherein the antigen is selected from the group consisting of tumor, viral, bacterial, and fungal antigens.

18. The composition of claim 13, wherein the engineered dendritic cell expresses the exogenous CCL-8, CCL-18, and CXCL-13.

19. The composition of claim 13, wherein the vectors are replication defective retroviruses, adenoviruses, or adeno-associated viruses.

20. An isolated engineered dendritic cell transduced with plasmids, cosmids, or viral vectors encoding exogenous CCL-8, CCL-18, and CXCL-13.

21. The engineered dendritic cell of claim 20, wherein the dendritic cell is further transduced with vectors encoding at least one exogenous chemokine selected from the group consisting of CCL-1, CCL-2, CCL-3, CCL-4, CCL-5, CCL-13, CCL-17, CCL-20, CCL-21, CXCL-9, CXCL-10, CXCL-11, CXCL-14, CXCL-16, and XCL1.

22. The engineered dendritic cell of claim 20, wherein the dendritic cell is selected from the group consisting of a $CD14^+$ blood monocyte-derived dendritic cell, a dermal or interstitial dendritic cell, a Langerhans cell, and a plasmacytoid dendritic cell.

23. The engineered dendritic cell of claim 20, wherein the dendritic cell is antigen-loaded.

24. The engineered dendritic cell of claim 23, wherein the antigen is selected from the group consisting of tumor, viral, bacterial, and fungal antigens.

25. The engineered dendritic cell of claim 20, wherein the dendritic cell expresses the exogenous CCL-8, CCL-18, and CXCL-13.

26. The engineered dendritic cell of claim 20, wherein the vectors are replication defective retroviruses, adenoviruses, or adeno-associated viruses.

* * * * *